(12) United States Patent
Starr et al.

(10) Patent No.: US 8,546,319 B2
(45) Date of Patent: Oct. 1, 2013

(54) USE OF P97 AS AN ENZYME DELIVERY SYSTEM FOR THE DELIVERY OF THERAPEUTIC LYSOSOMAL ENZYMES

(75) Inventors: Christopher M. Starr, Sonoma, CA (US); Todd Zankel, Novato, CA (US)

(73) Assignee: biOasis Advanced Technologies Inc., Victoria (CA)

(*) Notice: Subject to any disclaimer, the term of this patent is extended or adjusted under 35 U.S.C. 154(b) by 406 days.

(21) Appl. No.: 12/729,792

(22) Filed: Mar. 23, 2010

(65) Prior Publication Data
US 2010/0303797 A1 Dec. 2, 2010

Related U.S. Application Data

(63) Continuation of application No. 10/501,028, filed as application No. PCT/US03/00894 on Jan. 10, 2003, now abandoned.

(60) Provisional application No. 60/347,758, filed on Jan. 11, 2002.

(51) Int. Cl.
*C07K 14/00* (2006.01)
*C12N 9/00* (2006.01)

(52) U.S. Cl.
USPC .............................. 514/1; 435/183; 530/350

(58) Field of Classification Search
USPC ............................ 514/1; 435/183; 530/350
See application file for complete search history.

(56) References Cited

U.S. PATENT DOCUMENTS

| | | | |
|---|---|---|---|
| 4,866,042 A | 9/1989 | Neuwelt | |
| 5,672,683 A | 9/1997 | Friden et al. | |
| 5,981,194 A | 11/1999 | Jefferies et al. | |
| 7,138,371 B2 | 11/2006 | DeFrees et al. | |
| 7,179,617 B2 | 2/2007 | DeFrees et al. | |
| 7,700,554 B2 * | 4/2010 | Beliveau et al. | 424/1.69 |
| 2002/0119095 A1 | 8/2002 | Gabathuler et al. | |
| 2003/0072761 A1 | 4/2003 | LeBowitz | |
| 2004/0055022 A1 * | 3/2004 | Cheng et al. | 800/3 |
| 2004/0137557 A1 | 7/2004 | DeFrees et al. | |
| 2005/0026823 A1 | 2/2005 | Zankel et al. | |
| 2005/0158296 A1 | 7/2005 | Starr et al. | |
| 2008/0014188 A1 | 1/2008 | Zankel et al. | |

FOREIGN PATENT DOCUMENTS

| | | |
|---|---|---|
| WO | 8904663 | 6/1989 |
| WO | 9401463 | 1/1994 |
| WO | 9823646 | 6/1998 |
| WO | WO 01/59459 | 8/2001 |
| WO | WO 02/13873 | 2/2002 |
| WO | 03009815 | 2/2003 |

OTHER PUBLICATIONS

Jolly et al. 1997. Lysosomal storage diseases of animals: an essay in comparative pathology. Vet. Pathol. 34: 527-548.*

WikiPedia Foundation, Inc. Sandhoff disease, http://en.wikipedia.org/wiki/Sandhoff_disease, Modified 2007; Printed Jan. 16, 2008.
Demeule, M., et al., "High transcytosis of melanotransferrin (P97) across the blood-barrier", Journal Neurochemistry, 2002, pp. 924-933, vol. 83.
Tang, Y., et al., "Directing adenovirus across the blood-brain barrier via melanotransferrin (P97) transcytosis pathway in an vitro model", Gene Therapy, 2007, pp. 523-532, vol. 14.
Karkan, D., et al., "A Unique Carrier for Delivery of Therapeutic Compounds beyond the Blood-Brain Barrier", Plos One, 2008, pp. 1-14, vol. 3, Issue 6, e2469.
Moroo, I., et al., "Identification of a Novel Route of Iron Transcytosis across the Mammalian Blood-Brain Barrier", Microcirculation, 2003, pp. 457-462, vol. 10.
Wu, D., et al., "Pharmacokinetics and brain uptake of biotinylated basic fibroblast growth factor conjugated to a blood-brain barrier drug delivery system", Journal of Drug Target, 2002, pp. 239-245, vol. 10, No. 3.
Qian, Z.M., et al., "Targeted drug delivery via the transferrin receptor-mediated endocytosis pathway", Pharmacol Rev, 2002, pp. 561-587, vol. 54, No. 4.
Song, B.W., et al., "Enhanced neuroprotective effects of basic fibroblast growth factor in regional brain ischemia after conjugation to a blood-brain barrier delivery vector", Journal of Pharmacol Exp Ther, 2002, pp. 605-610, vol. 301, No. 2.
Moos ,T. and Morgan, E.H., "Restricted transport of anti-transferrin receptor antibody (OX26) through the blood-brain barrier in the rat", Journal of Neurochemistry, 2001, pp. 119-129, vol. 79, No. 1.
Endo, N. et al., "In-Vitro Cytotoxicity of a Human Serum Albumin-mediated Conjugate of Methotrexate with Anti-MM46 Monoclonal Antibody", Cancer Research, 1987, pp. 1076-1080, vol. 47, No. 4.
Aktas, Y., et al., "Development and brain delivery of chitosan-PEG nanoparticles functionalized with the monoclonal antibody OX26", Bioconjugate Chem., 2005, pp. 1503-1511, vol. 16, No. 6.
Bickel, U., et al., "Pharmacologic effects in vivo in brain by vector-mediated peptide drug delivery", Proc Natl Acad Sci., 1993, pp. 2618-2622, vol. 90, No. 7.
Bickel, U., et al., "In vivo demonstration of subcellular localization of anti-transferrin receptor monoclonal antibody-colloidal gold conjugate in brain capillary endothelium", The Journal of Histochemistry and Cytochemistry, 1994, pp. 1493-1497, vol. 42, No. 11.
Bickel, U., et al., "In vivo cleavability of a disulfide-based chimeric opioid peptide in rat brain", Bioconjugate Chem., 1995, pp. 211-218, vol. 6, No. 2.
Bickel, U., et al., "Delivery of peptides and proteins through the blood-brain barrier", Advanced Drug Delivery Reviews, 2001, pp. 247-279, vol. 46, No. 1-3.
Boado, R.J., et al., "Cloning and expression in *Pichia pastoris* of a genetically engineered single chain antibody against the rat transferrin receptor", Journal of Drug Targeting, 2000, pp. 403-412, vol. 8, No. 6.

(Continued)

*Primary Examiner* — Karen Cochrane Carlson

(57) ABSTRACT

The present invention provides for compositions and methods for treating, ameliorating or preventing a lysosomal storage disease by administering to a patient suffering from a lysosomal storage disease a P97 conjugated with an enzyme which is capable of transportation into the lysosomes of cells on either sides of the blood brain barrier.

10 Claims, 3 Drawing Sheets

(56) References Cited

OTHER PUBLICATIONS

Broadwell, R.D., et al., "Transcytosis of protein through the mammalian cerebral epithelium and endothelium. III. Receptor-mediated transcytosis through the blood-brain barrier of blood-borne transferrin and antibody against the transferrin receptor", Experimental Neurology, 1996, pp. 47-65, vol. 142, No. 1.

Cerletti A, et al., "Endocytosis and transcytosis of an immunoliposome-based brain drug delivery system", Journal of Drug Targeting, 2000, pp. 435-446, vol. 8, No. 6.

Deguchi, Y., et al., "Retention of biologic activity of human epidermal growth factor following conjugation to a blood-brain barrier drug delivery vector via an extended poly (ethylene glycol) linker", Bioconjugate Chem., 1999, pp. 32-37, vol. 10, No. 1.

Friden, P.M., "Anti-transferrin receptor antibody and antibody-drug conjugates cross the blood-brain barrier", Proc. Natl. Acad. Sci. USA, 1991, pp. 4771-4775, vol. 88, No. 11.

Gosk, S., et al., "Targeting anti-transferrin receptor antibody (OX26) and OX26-conjugated liposomes to brain capillary endothelial cells using in situ perfusion", Journal of Cerebral Blood Flow & Metabolism, 2004, pp. 1193-1204, vol. 24, No. 11.

Huwyler, J., et al., "Receptor mediated delivery of daunomycin using immunoliposomes: pharmacokinetics and tissue distribution in the rat", The Journal of Pharmacology and Experimental Therapeutics, 1997, pp. 1541-1546, vol. 282, No. 3.

Jefferies, W.A., et al., "Analysis of lymphopoietic stem cells with a monoclonal antibody to the rat transferrin receptor", Immunology, 1985, pp. 333-341, vol. 54, No. 2.

Jefferies, W.A., et al., "Transferrin receptor on endothelium of brain capillaries", Nature, 1984, pp. 162-163, vol. 312.

Kang, Y.S., and Pardridge, W.M., "Use of neutral avidin improves pharmacokinetics and brain delivery of biotin bound to an avidin-monoclonal antibody conjugate", The Journal of Pharmacology and Experimental Therapeutics, 1994, pp. 344-350, vol. 269, No. 1.

Kang, Y.S., et al., "Pharmacokinetics and organ clearance of a 3'-biotinylated, internally [32P]-labeled phosphodiester oligodeoxynucleotide coupled to a neutral avidin/monoclonal antibody conjugate", Drug Metabolism and Disposition, 1995, pp. 55-59, vol. 23, No. 1.

Kang, Y.S., et al., "Stability of the disulfide bond in an avidin-biotin linked chimeric peptide during in vivo transcytosis through brain endothelial cells", Journal of Drug Targeting, 2000, pp. 425-434, vol. 8, No. 6.

Kurihara, A. and Pardridge, W.M., "Aβ1-40 Peptide radiopharmaceuticals for brain amyloid imaging: III-In chelation, conjugation to poly(ethylene glycol)-biotin linkers, and autoradiography with Alzheimer's disease brain sections", Bioconjugate Chem., 2000, pp. 380-386, vol. 11.

Muraszko K, et al., "Pharmacokinetics and toxicology of immunotoxins administered into the subarachnoid space in nonhuman primates and rodents", Cancer Research, 1993, pp. 3752-3757, vol. 53, No. 16.

Muruganandam, A., et al., "Selection of phage-displayed llama single-domain antibodies that transmigrate across human blood-brain barrier endothelium", The FASEB Journal, 2001, pp. 1-22.

Pardridge, W.M., et al., "Vector-mediated delivery of a polyamide ("peptide") nucleic acid analogue through the blood-brain barrier in vivo", Proc. Natl. Acad. Sci. USA, 1995, pp. 5592-5596, vol. 92, No. 12.

Pardridge, W.M., et al., "Transport of human recombinant brain-derived neurotrophic factor (BDNF) through the rat blood-brain barrier in vivo using vector-mediated peptide drug delivery", Pharmaceutical Research, 1994, pp. 738-746, vol. 11, No. 5.

Saito, Y., et al., "Vector-mediated delivery of 125I-labeled beta-amyloid peptide Aβ1-40 through the blood-brain barrier and binding to Alzheimer disease amyloid of the Aβ1-40 /vector complex", Proc. Natl. Acad. Sci. USA, 1995, pp. 10227-10231, vol. 92, No. 22.

Shi, N., and Pardridge, W.M., "Noninvasive gene targeting to the brain", Proc. Natl. Acad. Sci. USA, 2000, po. 7567-7572, vol. 97, No. 13.

Skarlatos, S., et al., "Transport of [125I]transferrin through the rat blood-brain barrier", Brain Research. 1995, pp. 164-171, vol. 683, No. 2.

Wu, D., and Pardridge W.M., "Central nervous system pharmacologic effect in conscious rats after intravenous injection of a biotinylated vasoactive intestinal peptide analog coupled to a blood-brain barrier drug delivery system", The Journal of Pharmacology and Experimental Therapeutics, 1996, pp. 77-83, vol. 279, No. 1.

Wu, D., et al., "Pharmacokinetics and blood-brain barrier transport of [3H]-biotinylated phosphorothioate oligodeoxynucleotide conjugated to a vector-mediated drug delivery system", The Journal of Pharmacology and Experimental Therapeutics, 1996, pp. 206-211, vol. 276, No. 1.

Yoshikawa, T., and Pardridge, W.M., "Biotin delivery to brain with a covalent conjugate of avidin and a monoclonal antibody to the transferrin receptor", The Journal of Pharmacology and Experimental Therapeutics, 1992, pp. 897-903, vol. 263 No. 2.

Zhang, Y., and Pardridge, W.M., "Conjugation of brain-derived neurotrophic factor to a blood-brain barrier drug targeting system enables neuroprotection in regional brain ischemia following intravenous injection of the neurotrophin", Brain Research, 2001, pp. 49-56, vol. 889, No. 1-2.

β-N-acetylhexosaminidase. EC 3.2.1.52.HTTP://www.chem.qmul.ac.uk/iubmb/enzyme/EC3/2/1/52.html. Printed Dec. 17, 2009.

L-iduronidase-EC 3.2.1.76. http://www.chem.qmul.ac.uk/iubmb/enzyme/EC3/2/1/76.html. Printed Feb. 17, 2009.

N-acetylglucosaminidase EC 3.2.1.96. http://www.chem.qmul.ac.uk/iubmb.enzyme.EC3/2/1/96.html. Printed Feb. 17, 2009.

Demeule, et al., "High transcytosis of melanotransferrin (P97) across the blood—brain barrier," Journal of Neurochemistry. 83:924-933, 2002.

Geuze, et al., "Possible Pathways for Lysosomal Enzyme Delivery," The Journal of Cell Biology. 101:2253-2262, 1985.

Parenti, "Treating lysosomal storage diseases with pharmacological chaperones: from concept to clinics," EMBO Mol Med. 1:268-279, 2009.

Stefano, et al., "In vitro and in vivo evaluation of a non-carbohydrate targeting platform for lysosomal proteins," Journal of Controlled Release. 135:113-118, 2009.

International Preliminary Examination Report, PCT/03/00894, Feb. 14, 2005.

International Search Report, PCT/US03/00894, Jul. 24, 2003.

Richardson, et al, "The uptake of iron and transferrin by the human malignant melanoma cell," Biochimica et Biophysica Acta, 1053, (1990), pp. 1-12.

Robinson, et al., "NSF is required for transport from early to late endosomes," Journal of Cell Science, 110, (1997), pp. 2079-2087.

* cited by examiner

A

Alexa Fluor 594-p97

B

Lysosensor Green

Overlay

C

SEQUENCE LISTING

```
<160> NUMBER OF SEQ ID NOS: 1

<210> SEQ ID NO 1
<211> LENGTH: 719
<212> TYPE: PRT
<213> ORGANISM: Homo sapiens

<400> SEQUENCE: 1

Gly Met Glu Val Arg Trp Cys Ala Thr Ser Asp Pro Glu Gln His Lys
1               5                   10                  15

Cys Gly Asn Met Ser Glu Ala Phe Arg Glu Ala Gly Ile Gln Pro Ser
            20                  25                  30

Leu Leu Cys Val Arg Gly Thr Ser Ala Asp His Cys Val Gln Leu Ile
        35                  40                  45

Ala Ala Gln Glu Ala Asp Ala Ile Thr Leu Asp Gly Gly Ala Ile Tyr
    50                  55                  60

Glu Ala Gly Lys Glu His Gly Leu Lys Pro Val Val Gly Glu Val Tyr
65                  70                  75                  80

Asp Gln Glu Val Gly Thr Ser Tyr Tyr Ala Val Ala Val Val Arg Arg
```

```
                    85                  90                  95
Ser Ser His Val Thr Ile Asp Thr Leu Lys Gly Val Lys Ser Cys His
                100                 105                 110
Thr Gly Ile Asn Arg Thr Val Gly Trp Asn Val Pro Val Gly Tyr Leu
                115                 120                 125
Val Glu Ser Gly Arg Leu Ser Val Met Gly Cys Asp Val Leu Lys Ala
                130                 135                 140
Val Ser Asp Tyr Phe Gly Gly Ser Cys Val Pro Gly Ala Gly Glu Thr
145                 150                 155                 160
Ser Tyr Ser Glu Ser Leu Cys Arg Leu Cys Arg Gly Asp Ser Ser Gly
                165                 170                 175
Glu Gly Val Cys Asp Lys Ser Pro Leu Glu Arg Tyr Tyr Asp Tyr Ser
                180                 185                 190
Gly Ala Phe Arg Cys Leu Ala Glu Gly Ala Gly Asp Val Ala Phe Val
                195                 200                 205
Lys His Ser Thr Val Leu Glu Asn Thr Asp Gly Lys Thr Leu Pro Ser
                210                 215                 220
Trp Gly Gln Ala Leu Leu Ser Gln Asp Phe Glu Leu Leu Cys Arg Asp
225                 230                 235                 240
Gly Ser Arg Ala Asp Val Thr Glu Trp Arg Gln Cys His Leu Ala Arg
                245                 250                 255
Val Pro Ala His Ala Val Val Val Arg Ala Asp Thr Asp Gly Gly Leu
                260                 265                 270
Ile Phe Arg Leu Leu Asn Glu Gly Gln Arg Leu Phe Ser His Glu Gly
                275                 280                 285
Ser Ser Phe Gln Met Phe Ser Ser Glu Ala Tyr Gly Gln Lys Asp Leu
                290                 295                 300
Leu Phe Lys Asp Ser Thr Ser Glu Leu Val Pro Ile Ala Thr Gln Thr
305                 310                 315                 320
Tyr Glu Ala Trp Leu Gly His Glu Tyr Leu His Ala Met Lys Gly Leu
                325                 330                 335
Leu Cys Asp Pro Asn Arg Leu Pro Pro Tyr Leu Arg Trp Cys Val Leu
                340                 345                 350
Ser Thr Pro Glu Ile Gln Lys Cys Gly Asp Met Ala Val Ala Phe Arg
                355                 360                 365
Arg Gln Arg Leu Lys Pro Glu Ile Gln Cys Val Ser Ala Lys Ser Pro
                370                 375                 380
Gln His Cys Met Glu Arg Ile Gln Ala Glu Gln Val Asp Ala Val Thr
385                 390                 395                 400
Leu Ser Gly Glu Asp Ile Tyr Thr Ala Gly Lys Lys Tyr Gly Leu Val
                405                 410                 415
Pro Ala Ala Gly Glu His Tyr Ala Pro Glu Asp Ser Ser Asn Ser Tyr
                420                 425                 430
Tyr Val Val Ala Val Val Arg Arg Asp Ser Ser His Ala Phe Thr Leu
                435                 440                 445
Asp Glu Leu Arg Gly Lys Arg Ser Cys His Ala Gly Phe Gly Ser Pro
450                 455                 460
Ala Gly Trp Asp Val Pro Val Gly Ala Leu Ile Gln Arg Gly Phe Ile
465                 470                 475                 480
Arg Pro Lys Asp Cys Asp Val Leu Thr Ala Val Ser Glu Phe Phe Asn
                485                 490                 495
Ala Ser Cys Val Pro Val Asn Asn Pro Lys Asn Tyr Pro Ser Ser Leu
                500                 505                 510
```

```
                    -continued
Cys Ala Leu Cys Val Gly Asp Glu Gln Gly Arg Asn Lys Cys Val Gly
        515                 520                 525

Asn Ser Gln Glu Arg Tyr Tyr Gly Tyr Arg Gly Ala Phe Arg Cys Leu
    530                 535                 540

Val Glu Asn Ala Gly Asp Val Ala Phe Val Arg His Thr Thr Val Phe
545                 550                 555                 560

Asp Asn Thr Asn Gly His Asn Ser Glu Pro Trp Ala Ala Glu Leu Arg
                565                 570                 575

Ser Glu Asp Tyr Glu Leu Leu Cys Pro Asn Gly Ala Arg Ala Glu Val
            580                 585                 590

Ser Gln Phe Ala Ala Cys Asn Leu Ala Gln Ile Pro Pro His Ala Val
        595                 600                 605

Met Val Arg Pro Asp Thr Asn Ile Phe Thr Val Tyr Gly Leu Leu Asp
    610                 615                 620

Lys Ala Gln Asp Leu Phe Gly Asp Asp His Asn Lys Asn Gly Phe Lys
625                 630                 635                 640

Met Phe Asp Ser Ser Asn Tyr His Gly Gln Asp Leu Leu Phe Lys Asp
                645                 650                 655

Ala Thr Val Arg Ala Val Pro Val Gly Glu Lys Thr Thr Tyr Arg Gly
            660                 665                 670

Trp Leu Gly Leu Asp Tyr Val Ala Ala Leu Glu Gly Met Ser Ser Gln
        675                 680                 685

Gln Cys Ser Gly Ala Ala Ala Pro Ala Pro Gly Ala Pro Leu Leu Pro
        690                 695                 700

Leu Leu Leu Pro Ala Leu Ala Ala Arg Leu Leu Pro Pro Ala Leu
705                 710                 715
```

USE OF P97 AS AN ENZYME DELIVERY SYSTEM FOR THE DELIVERY OF THERAPEUTIC LYSOSOMAL ENZYMES

CROSS-REFERENCES TO RELATED APPLICATIONS

This application is a continuation of U.S. application Ser. No. 10/501,028 filed Mar. 14, 2005, which is a national phase entry application of PCT/US2003/00894 filed Jan. 10, 2003 (which designated the U.S.) which claims the benefit of U.S. Provisional application serial no. 60/347,758 filed Jan. 11, 2002 (now abandoned). All of the prior applications are incorporated by reference herein in their entirety.

STATEMENT REGARDING SEQUENCE LISTING

The Sequence Listing associated with this application is provided in text format in lieu of a paper copy, and is hereby incorporated by reference into the specification. The name of the text file containing the Sequence Listing is BIOA_001_02US_ST25.txt. The text file is 7 KB, was created on Sep. 18, 2012, and is being submitted electronically via EFS-Web.

FIELD OF THE INVENTION

The present invention is related to the field of pharmaceutics and specifically to treatment of diseases through the introduction of p97 protein or polypeptide conjugated to a therapeutic or diagnostic agent to a subject. In particular, this invention relates to conjugates of p97 and proteins deficient in a lysosomal storage disease and methods for the treatment, amelioration or prevention of lysosomal storage diseases by administration of the conjugates to subjects having such diseases.

BACKGROUND OF THE INVENTION

Lysosomal storage diseases (LSDs) result from the absence or reduced activity of specific enzymes within the lysosomes of a cell. A large number of these enzymes have been identified and correlated with their related diseases. Once the missing or deficient enzyme has been identified, treatment can be reduced to the problem of delivering replacement enzyme (drug) to a patient's affected tissues. Within cells, the effect of the missing enzyme can be seen as an accumulation of undegraded "storage material" within the intracellular lysosome. This build-up causes lysosomes to swell and malfunction, resulting in cellular and tissue damage. As lysosomal storage diseases typically have a genetic etiology, many tissues will lack the enzyme in question. However, different tissues suffer the absence of the same enzyme differently. How adversely a tissue will be affected is determined, to some extent, by the degree to which that tissue generates the substrate of the missing enzyme. The types of tissue most burdened by storage, in turn, dictate how the drug should be administered to the patient. While intravenous enzyme replacement therapy (ERT) is beneficial for LSDs (e.g. MPS I, MPS II), means for enhancing the delivery of the therapeutic enzyme to the lysosome in such diseases would be advantageous in terms of reduced cost and increased therapeutic efficacy.

In addition, the blood-brain barrier (BBB) blocks the free transfer of many agents from blood to brain. For this reason, LSDs that present with significant neurological affect (e.g. MPS III, MLD, GM1) are not expected to be as responsive to intravenous ERT. For such diseases, a method of delivering the enzyme across the BBB and into the lysosomes of the affected cells would be highly desirable.

In the early 1980's, melanotransferrin (MTf) or p97 was identified as an oncofetal antigen that was either not expressed, or only slightly expressed in normal tissues, but was found in much larger amounts in neoplastic cells (especially malignant melanoma cells) and fetal tissues (Woodbury, et al., *P.N.A.S. USA,* 77:2183-2187 (1980)). More recently, there have been additional reports of human MTf being identified in normal tissues, including sweat gland ducts, liver endothelial cells and the endothelium and reactive microglia of the brain (Jefferies, et al., *Brain Res.,* 712:122-126 (1996); and Rothenberger, et al., *Brain Res.,* 712:117-121 (1996)). Interestingly, normal serum contains very low levels of soluble circulating MTf, but increased soluble serum MTf has been found in patients with advanced Alzheimer's Disease (Kennard, et al., *Nat. Med.,* 2:1230-1235 (1996); U.S. Pat. No. 5,981,194).

The biochemical role and metabolism of MTf has proven difficult to elucidate. Based on appearances, MFt is deceptively similar to transferrin (Tf) and lactotransferrin (lactoferrin or Lf). In humans, these proteins share a 37-39% amino acid sequence homology. In particular, each of these proteins reversibly binds iron, and their N-terminal iron binding domains are quite similar (Baker, et al., *TIBS,* 12:350-353 (1987)).

However, functional parallels between these proteins have not been confirmed. For one thing, unlike Tf and Lf, MTf exists in both a membrane bound form and a serum soluble form. Further, in contrast to Tf and Lf, no cellular receptor for MTf has been identified. Serum soluble Tf is known to be taken into cells in an energy-dependent process mediated by the transferrin receptor (Tf-R) (Cook, et al., *Annu. Rev. Med.,* 44:63-74) (1993)). Lf internalization is also likely to be mediated by a receptor mediated process (Fillebeen, et al., *J. Biol. Chem.,* 274(11):701-7017 (1999)). Two known receptors for Lf are LRP-1 and RAGE, although others may exist (Melinger, et al., *FEBS Letters,* 360:70-74 (1995); Schmidt, *J. Biol. Chem.,* 269(13):9882-9888 (1994).

With respect to the central nervous system (e.g., brain, spinal cord), there are at least three ways to enhance delivery: direct injection, permeabilization of the BBB, and modification of the drug. Direct injection involves injection of drug into brain tissue, bypassing the vasculature completely. This method suffers primarily from the risk of complications (infection, tissue damage) incurred by intra-cranial injections. This risk is compounded when considered in the context of a regular treatment regimen applied over the course of to the patient's life. It is also difficult, using a limited number of single site injections, to match the penetration that blood vessels (and hence, potentially, drug) have throughout the brain.

The second method entails non-specifically compromising the BBB with concomitant injection of intravenous drug. Permeabilization of the BBB is accomplished chemically. This method suffers from a lack of specificity. All those components in the blood that are necessarily excluded by the BBB will enter the brain along with the drug. The brain is left vulnerable under these conditions and damage would be anticipated over the course of a life-long regimen of treatment.

The third means of increasing brain availability of blood borne drug entails specific functionalization of the drug with moieties that facilitate transport through an uncompromised BBB. This method has the advantages of specific BBB infiltration and convenient intravenous administration. A method of increasing the ability of a therapeutic agent to cross the blood brain barrier is taught in U.S. Pat. No. 6,455,494, incorporated herein by reference its entirety, which discloses the use of p97 as a carrier for delivering a therapeutic drug across the blood brain barrier.

p97 (melanotransferrin) is a naturally occurring human protein. p97 was discovered and characterized as a cell surface marker for human melanoma (melanoma-associated antigen), but has more recently been found in other tumor types, as well as in normal human brain and liver tissue, in trace amounts in other body tissues and in serum. The role of p97 in the body is unknown, but based on its structure and binding properties, it is thought to be involved in the transport of metal ions (e.g. iron) into cells. Jefferies, et al. have been working with p97 since 1992 (U.S. Pat. No. 5,981,194). These investigations have focused on p97 as a diagnostic marker for Alzheimer's disease (AD). Synapse has developed a blood (serum) test for AD that is based on the finding that the p97 serum level increases with the progression of the disease. During the development of this test, it was discovered that p97 is actively transported from the blood into the brain tissue of normal individuals. This discovery was the impetus for the development of p97 as a potential transport system to deliver molecules from the blood, across the BBB to reach brain interstitial fluids.

The key event for the successful delivery of therapeutic agents into brain is the transport of these large molecules across the tight network of capillary endothelial cells that comprise the BBB. During the last few years, it has been demonstrated both in vitro and in animal models that small synthetic molecules, large glycoprotein enzymes, and large inorganic particles (5 nm colloidal gold particles) chemically linked to p97, can be transported across the BBB to brain cells. Such transport of large molecules across the BBB involves a process known as transcytosis. This is a mechanism whereby molecules are picked up from the blood and transported through the capillary cells of the otherwise intact BBB to the brain tissue.

Transcytosis pathways are distinct from other vesicular traffic within the capillary endothelial cell and transit occurs without alteration of the transported materials. Transcytosis is a cell-type specific process mediated by receptors on the BBB endothelial surface. The transport of p97-conjugates (i.e., p97 chemically linked to macromolecules) across the BBB occurs by transcytosis. p97 conjugated to the enzyme horseradish peroxidase (HRP) (an example of an enzyme "payload") can be transported across the BBB.

For an effective treatment of LSDs, a therapeutic agent (e.g., the deficient enzyme, or another enzyme or protein having a desired therapeutic or missing enzyme activity) must be taken up by the affected cells and routed to the lysosome where it acts upon the excessive or harmful amount of storage material residing therein. Applicants provide below compositions and methods for treating LSDs involving the use of p97 proteins to target delivery of therapeutic agents, including proteins or enzymes deficient in LSDs, to the lysosomes of cells.

BRIEF SUMMARY OF THE INVENTION

The present invention is related to the discovery that conjugates of p97 and a therapeutic agent, in which the agent is covalently linked to p97, or to a fragment or protion thereof, are excellent vehicles for the enhanced delivery of the agent to lysosomes of cells within and without the CNS. In a first aspect, therefore the invention provides a method of delivering a therapeutic agent to the lysosome of a cell. In a second aspect the invention provides a method of treating a lysosomal storage disease in a patient by administering a p97 molecule covalently linked to a therapeutic agent which is a protein or enzyme deficient in the lysosomes of a subject having such a disease (e.g., enzyme replacement therapy). Such p97-agent conjugates are particularly useful, for example, in the treatment of lysosomal storage diseases such as MPS I, MPS II, MPS III A, MPS III B, Metachromatic Leukodystrophy, Gaucher, Krabbe, Pompe, CLN2, Niemann-Pick and Tay-Sachs disease wherein a lysosomal protein deficiency contributes to the disease state. In a third aspect, the invention provides pharmaceutical compositions comprising a p97 molecule covalently linked to a protein or enzyme deficient in a lysosomal storage disease. In a fourth aspect, the invention provides methods for identifying p97 conjugates which are useful in delivering an agent to a lysosome.

In some embodiments, the methods of the invention can be used to treat such lysosomal storage diseases as Aspartylglucosaminuria, Cholesterol ester storage disease/Wolman disease, Cystinosis, Danon disease, Fabry disease, Farber Lipogranulomatosis/Farber disease, Fucosidosis, Galactosialidosis types I/II, Gaucher disease types I/IIIII Gaucher disease, Globoid cell leucodystrophy/Krabbe disease, Glycogen storage disease II/Pompe disease, GM1-Gangliosidosis types I/II/III, GM2-Gangliosidosis type I/Tay Sachs disease, GM2-Gangliosidosis type II Sandhoff disease, GM2-Gangliosidosis, α-Mannosidosis types I/II, β-Mannosidosis, Metachromatic leucodystrophy, Mucolipidosis type I/Sialidosis types I/II Mucolipidosis types II/III I-cell disease, Mucolipidosis type IIIC pseudo-Hurler polydystrophy, Mucopolysaccharidosis type I, Mucopolysaccharidosis type II Hunter syndrome, Mucopolysaccharidosis type IIIA Sanfilippo syndrome, Mucopolysaccharidosis type IIIB Sanfilippo syndrome, Mucopolysaccharidosis type IIIC Sanfilippo syndrome, Mucopolysaccharidosis type IIID Sanfilippo syndrome, Mucopolysaccharidosis type IVA Morquio syndrome, Mucopolysaccharidosis type IVB Morquio syndrome, Mucopolysaccharidosis type VI, Mucopolysaccharidosis type VII Sly syndrome, Mucopolysaccharidosis type IX, Multiple sulphatase deficiency, Neuronal Ceroid Lipofuscinosis, CLN1 Batten disease, Neuronal Ceroid Lipofuscinosis, CLN2 Batten disease, Niemann-Pick disease types AB Niemann-Pick disease, Niemann-Pick disease type C1 Niemann-Pick disease, Niemann-Pick disease type C2 Niemann-Pick disease, Pycnodysostosis, Schindler disease types I/II Schindler disease, and Sialic acid storage disease.

In some embodiments, the p97 conjugates compositions comprise from about 1 to about 5 molecules of the agent of interest linked to a single p97 molecule. In some embodiments, more that one agent of interest may be linked to a single p97 molecule. Selective biodistribution of p97-agents can enhance the selective targeting of p97-linked agents to specific organs.

In addition, the present invention provides screening assays for identifying p97-agent conjugates that can prevent, amelioriate, or treat a lysosomal storage disease by contacting a cell containing a lysosome with the conjugate and determining whether the conjugate delivers the agent to the lysosome. The delivery can be assessed by labeling the conjugate and then monitoring or detecting the location of the label in the cell or by determining the effect of the conjugate on the amount of the storage material found in the lysosome. In a preferred embodiment, the agent is a protein or enzyme deficient in the lysosomal storage disease. In another embodiment, the cell is deficient in the agent conjugated to the p97 molecule.

In some embodiments, the method treats lysosomal storage diseases wherein the tissues to be treated are isolated from the circulatory system by the blood brain barrier (e.g., the brain). In one embodiment, the present invention provides a method for delivering a compound of interest through the blood-brain barrier of a subject into a lysosome of a cell of the subject comprising: administering a conjugated agent to the subject, wherein the conjugated agent comprises a melanotransferrin linked to the agent via a linker; whereby the conjugated agent passes through the blood-brain barrier of the subject, and whereby the agent enters into a lysosome of a cell of the subject.

In another embodiment, the present invention provides for a method for treating, ameliorating, or preventing a lysosomal storage disease of a subject comprising: administering a conjugated agent to a subject, wherein the conjugated agent comprises a melanotransferrin linked to an agent of interest via a linker; whereby the agent enters into a lysosome of a peripheral cell (e.g., non-CNS cell) of the subject.

In still another embodiment, the present invention provides for a method of enzyme replacement therapy comprising: administering a conjugated agent to a subject in need of the enzyme replacement therapy, wherein the conjugated agent comprises a melanotransferrin linked to an enzyme via a linker, wherein the cells of the patient have lysosomes which contain insufficient amounts of the enzyme to prevent or reduce damage to the cells; whereby the conjugated agent passes through the blood-brain barrier of the subject, and whereby sufficient amounts of the enzyme enter the lysosomes to prevent or reduce damage to the cells.

In even another embodiment, the present invention provides a method for treating a patient suffering from a lysosomal storage disease resulting from the absence of an enzyme within the lysosomes of a cell found in the brain comprising: administering to the patient a conjugated agent, wherein the conjugated agent comprises p97 linked to the enzyme via a linker; whereby the conjugated agent passes through the blood-brain barrier of the patient, and whereby sufficient amounts of the enzyme enter the lysosomes to prevent or reduce damage to the cells.

In yet even another embodiment, the present invention provides for a method for identifying an agent that can prevent, ameliorate or treat a lysosomal storage disease, comprising: administering a p97-conjugated agent to a cell, wherein absence of the enzyme causes the lysosomal storage disease; and determining whether the agent reduces damage to the cell compared to damage to the cell if the conjugated agent was not administered to the cell. In certain embodiments, the method is a high throughput assay.

In a further embodiment, the present invention provides for a novel composition comprising a conjugated agent, wherein the conjugated agent comprises a p97 molecule linked to an enzyme via a linker, wherein the enzyme is an enzyme, such as those set forth herein, found in the lysosomes of cells contained within the BBB. The composition can further comprise a suitable pharmaceutical carrier.

Further, the present invention provides a lysosome comprising the conjugated agent. The present invention also provides a cell comprising a lysosome comprising the conjugated agent. Preferably, the cell is a cell found surrounded by a blood-brain barrier. More preferably, the cell is a neuron or a brain cell.

In some embodiments, the p97-agent conjugate comprises any one of the following proteins as the active agent covalently linked to a p97 molecule: aspartylglucosaminidase, acid lipase, cysteine transporter, Lamp-2, α-galactosidase A, acid ceramidase, α-L-fucosidase, β-hexosaminidase A, GM2-activator deficiency, α-D-mannosidase, β-D-mannosidase, arylsulphatase A, saposin B, neuraminidase, α-N-acetylglucosaminidase phosphotransferase, phosphotransferase γ-subunit, L-iduronidase, iduronate-2-sulphatase, heparan-N-sulphatase, α-N-acetylglucosaminidase, acetyl-CoA:N-acetyltransferase, N-acetylglucosamine 6-sulphatase, galactose 6-sulphatase, β-galactosidase, N-acetylgalactosamine 4-sulphatase, hyaluronoglucosaminidase, multiple sulphatases, palmitoyl protein thioesterase, tripeptidyl peptidase I, acid sphingomyelinase, cholesterol trafficking, cathepsin K, α-galactosidase B, sialic acid transporter. In some embodiments, the agent is a protein of human or mammalian sequence, origin or derivation. The p97 protein or fragment can also be of human or mammalian sequence, origin or derivation.

DETAILED DESCRIPTION OF THE INVENTION

I. Introduction

Figure 1:
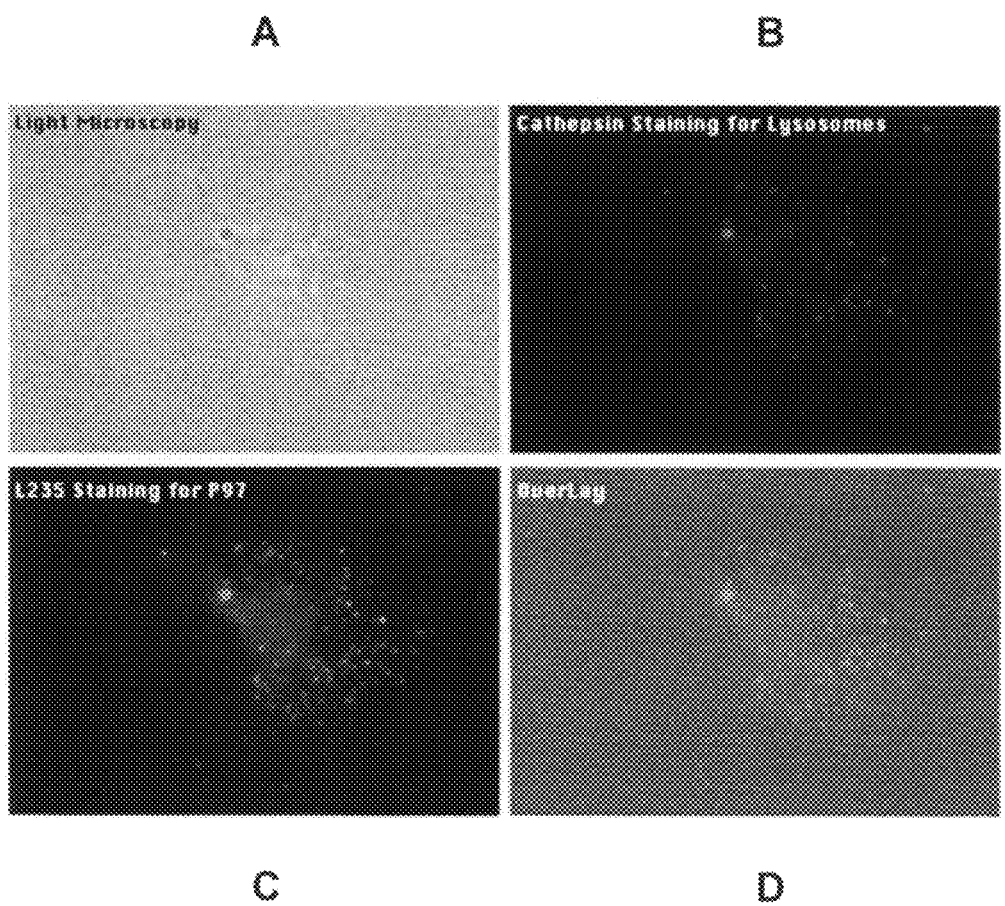
FIGS. 1A-1D depict human hNT neurons (derived from human teratocarcinoma) stained with anti-Cathepsin L and the L235 monoclonal antibody to p97 (see, Example 1 for details).

The present invention generally provides methods and compositions for enhanced delivery of the lysosomal storage disease related agents to the lysosomes of cells affected by a lysosomal storage disease. The invention relates to the surprising discovery that MTf or p97 proteins and fragments thereof not only undergo transcytosis across the blood brain barrier but also are transported into lysosomes. As a result, p97 molecules which are demonstrated vehicles for delivering agents across the blood brain barrier are also surprisingly particularly useful also as a means of delivering deficient proteins or enzymes to lysosomes for the treatment of lysosomal storage diseases resulting from such deficiencies.

The conjugate agents of the present invention offer many important advantages in the treatment of lysosomal storage diseases. The MTf or p97 is a natural compound usually found in human cells at different levels. Because p97 is a natural protein of humans, it is unlikely to result in immunological hyper-responsiveness, as it is frequently the case with the use of Mab therapies making them is refractory for use in repeated injections.

In terms of drug delivery, the p97 system can cross the BBB quickly (within an hour), and is metabolized within 12 hours, thus it is efficiently eliminated from tissues. These features provide the chance of repetitive injections without saturation of the receptors.

Moreover, p97 does not compete with endogenous transferrin whose amount is estimated to be 10,000 times higher than serum p97. Thus transferring will not compete with the method of delivering therapeutic agents by covalently or otherwise linking them to p97. The protein p97 shows little toxicity if any. The p97 protein is biodegradable and will not circulate for long periods of time. The protein has a demonstrated capacity to cross the BBB and due to its affinity for the endothelial cells lining the vascular bed of the brain, p97 vector is particularly useful for delivering a conjugated or otherwise bound agent to lysosomes located within the brain tissue.

II. Definitions

Unless otherwise defined, all technical and scientific terms used herein have the same meaning as commonly understood by one of ordinary skill in the art to which this invention belongs. Each publication, patent application, patent, and other reference cited herein is incorporated by reference in its entirety to the extent that it is not inconsistent with the present disclosure.

It is noted here that as used in this specification and the appended claims, the singular forms "a," "an," and "the" include plural reference unless the context clearly dictates otherwise.

MTf or p97 includes membrane bound p97 (i.e., p97 attached to a GPI anchor or some other anchor), secreted p9'7, soluble p97, cleaved p97, analogs of p97 which are functional equivalents of p97 (having generally greater than 40%, 60%, 80%, 90% or 95% homology of their corresponding amino acid sequences and including allelic variants of p97), human, mouse, chicken and/or rabbit p97, and derivatives, portions, or fragments thereof. The p97 can be in the form of acidic or basic salts, or in its neutral form. In addition, individual amino acid residues can be modified, such as by oxidation or reduction. Moreover, various substitutions, deletions, or additions can be made to the amino acid or nucleic acid sequences, the net effect of which is to retain or improve upon the desired biological activity of p97. Due to code degeneracy, for example, there may be considerable variation in nucleotide sequences encoding the same amino acid sequence. Further characterization of p97, including the complete amino acid sequence of p97, is found in U.S. Pat. No. 5,981,194.

A p97 fragment as used herein includes any portion of p97 or its biologically equivalent analogs that contains a sufficient portion of p97 to enable it to bind to the MTf or the LRP1 or LRP1B receptor and to be transported across the blood-barrier; or that otherwise retains or improves upon the desired biological activities of p97 in the transcytosis and/or delivery of an agent to the lysosome.

Additional teachings regarding the making and using of p97 as diagnostic and therapeutic agents is found in International Application No. PCT/CA93/00272 and U.S. Pat. No. 5,981,194, the disclosures of which are incorporated by reference in their entirety.

"Modulate," as used herein, refers to the ability to alter, by increase or decrease (e.g., to act as an antagonist or agonist).

"Melanotransferrin receptor" ("MTf-R"), as used herein, refers to any biological system that specifically or preferentially binds MTf. This term is intended to include those receptors which competitively bind Lf and/or β-amyloid protein, but excludes those receptors which are specific for Tf such as the transferrin receptor (Tf-R) (which is described at OMIM #*190010, and which is also known as TFR, TRFR and CD71). A receptor known to specifically or preferentially bind Lf is herein called a "lactotransferrin receptor" (Lf-R). Known Lf-Rs include, but are not limited to, the LDL-related receptors. A known LDL-related receptor is lipoprotein receptor-related protein/alpha2-macroglobulin receptor ("LRP1"). The term MTf-R specifically includes other receptors found on endothelial cells that specifically bind both MTf and Lf, but not Tf. In a preferred embodiment, the MTf-R is the LRP1. In a more preferred embodiment, the MTf-R is LRP1B.

Members of the low density lipoprotein (LDL) receptor family include LDL-R (132 kDa); LRP/LRP1 and LRP1B (600 kDa); Megalin ((LRP2), 600 kDa); VLDL-R (130 kDa); ER-2 (LRP-8, 130 kDa); Mosaic LDL-R (LR11, 250 KDa); and other members such as LRP3, LRP6, and LRP-7. Characteristic features of the LDL-R family include cell-surface expression; extracellular ligand binding domain repeats (DxSDE); requirement of Ca++ for ligand binding; recognition of RAP and ApoE; EGF precursor homology domain repeats (YWTD); single membrane spanning region; internalization signal in the cytoplasmic domain (FDNPXY); and receptor mediated endocytosis of various ligands.

LRP refers to the low density lipoprotein receptor related protein and members of this receptor family. LRP is a large protein of 4525 amino acids (600 kDa) which is cleaved by furin to produce two subunits of 515-(α) and 85-(β) kDa that remain non-covalently bound. LRP is mainly expressed in the liver, kidney, neuron, CNS, BBB, SMC and various cultured cells.

LRP ligands refer to a number of molecules that are known to bind LRP. These molecules include, for instance, lactoferrin, RAP, lipoprotein lipase, ApoE, Factor VIII, β-amyloid precursor, α2-macroglobulin, thrombospondin 2 MMP-2, MPP-9-TIMP-1; uPA:PAI-I:uPAR; and tPA:PAI-1:uPAR.

LRP 1B is a recently discovered member of the low density lipoprotein receptor family. 600 kDa multifunctional cell surface receptor. See Liu et al., *J. Biol. Chem.* 276 (31):28889-28896 (2001). See also Liu et al., *Genomics* 69, 271-274 (2000); and Liu et al., *Cancer Res.* 60, 1961-1967 (2000). This receptor is more closely related to LRP than megalin and shares a 59% homology at cDNA level and a 52% homology at predicted amino acid level. the LRP 1B gene is expressed in the brain, thyroid and salivary gland. Known ligands for LRP 1B include RAP, tPA, PAI-1.

Mouse LRP1B is accessible through GenBank Accession Nos. XM 143023 XM 130241. Human LRP1B is accessible through GenBank Accession Nos. XM 015452.

"Lipoprotein receptor-related protein/alpha2-macroglobulin receptor" ("LRP1"), as used herein, refers to a multifunctional receptor. It is believed that the clustering of cysteine-rich type. A binding repeats, resembling those found in the LDL receptor, is the molecular principle for the ability to bind a variety of ligands that were previously thought to be unrelated: activated alpha-2-macroglobulin, apolipoprotein E, lipoprotein lipase, plasminogen activators and complexes with their inhibitor (PA and PA/PAI-1), lipoprotein (a), pseudomonas exotoxin A, human rhinovirus, Lf and the so-called receptor associated protein (RAP). See, Meilinger, et al., FEBS Let., 360:70-74 (1995). LRPI is accessible through GenBank Accession No.: X 13916 and Swiss-Prot Primary Accession No.: Q07954. Alternative names for the LRP1 gene/protein include: Low-density lipoprotein receptor-related protein 1 [precursor], LRP, Alpha-2-macroglobulin receptor, A2MR, Apolipoprotein E receptor, APOER, CD91, LRP1 or A2MR.

Figure 3:
FIG. 3 shows the general construct of a p97-conjugate covalently conjugated to an agent.

A "p97-conjugate" refers to a composition comprising p97, or a fragment thereof, covalently conjugated to an agent. The conjugation may be direct or indirect (i.e., through an extended linker) so long as it is a chemical conjugation. The general construct of the composition of the invention is shown in FIG. 3.

The agent may serve a therapeutic or prophylactic purpose in the treatment of a lysosomal storage disease in mammals, and particularly, humans.

"Increasing relative delivery" as used herein refers to the effect whereby the accumulation at the lysosome of a p97-conjugated agent is increased relative to the accumulation of the original agent.

"Therapeutic index" refers to the dose range (amount and/or timing) above the minimum therapeutic amount and below an unacceptably toxic amount.

"Equivalent dose" refers to a dose which contains the same amount of active agent.

The p97-agent conjugate can comprise one or more agent moieties (e.g., 1 to 10 or 1 to 4 or 2 to 3 moieties) linked to p97. For example, conjugation reactions may conjugate from 1 to 4 or more molecules of alpha-L-iduronidase to a single p97 molecule. These formulations can be employed as mixtures, or they may be purified into specific p97:agent (mol:mol) formulations. Those skilled in the art are able to determine which format and which mol:mol ratio is preferred. Further, mixtures of agents may be linked to p97 to facilitate a more complete degradation of the stored substrates. These p97-agents may consist of a range of mol:mol ratios. These, too, may be separated into purified mixtures or they may be employed in aggregate.

The p97 conjugated agents can enter or be transported into or end up residing in the lysosomes of a cell within or without the CNS. The rate of passage of the conjugated agent can be modulated by any compound or protein that can modulate a MTf receptor activity. Methods for identifying or determining such a modulator are disclosed in U.S. Provisional Patent Application No. 60/308,002 and U.S. patent application Ser. No. 10/206,448, filed on Jul. 25, 2002, the disclosures of which are incorporated by reference in their entirety. The cell can be from any tissue or organ system affected by the lysosomal storage disease. The cell can be, for instance, an endothelial, epithelial, muscle, heart, bone, lung, fat, kidney, or liver cell. In some embodiments, the cell is preferably a cell found within the BBB. In some embodiments, the cell is a neuron or a brain cell. In other embodiments, the cell is a cell of the periphery or one which is not isolated from the general circulation by an endothelium such as that of the BBB.

The agent can be a protein or enzyme or any fragment of such that still retains some, substantially all, or all of the activity of the enzyme. In some embodiments, the protein or enzyme is one that, if not expressed or produced or if substantially reduced in expression or production, would give rise to a lysosomal storage disease. Preferably, the protein or enzyme is derived or obtained from a human or mouse. In some embodiments, in the treatment of human LSDs, the p97-agent conjugate comprises a protein or enzyme that is deficient in the lysosomal storage enzyme deficient in subject or patient to be treated. Such enzymes, include for example, α-L-iduronidase, iduronate-2-sulfatase, heparan N-sulfatase, α-N-acetylglucosaminidase, Arylsulfatase A, Galactosylceramidase, acid-alpha-glucosidase, thioesterase, hexosaminidase A, Acid Spingomyelinase, α-galactosidase, or any other lysosomal storage enzyme. A table of lysosomal storage diseases and the proteins deficient therein follows:

| Lysosomal Storage Disease | Protein deficiency |
|---|---|
| Mucopolysaccharidosis type I | L-Iduronidase |
| Mucopolysaccharidosis type II Hunter syndrome | Iduronate-2-sulphatase |
| Mucopolysaccharidosis type IIIA Sanfilippo syndrome | Heparan-N-sulphatase |
| Mucopolysaccharidosis type IIIB Sanfilippo syndrome | α-N-Acetylglucosaminidase |
| Mucopolysaccharidosis type IIIC Sanfilippo syndrome | AcetylCoA:N-acetyltransferase |
| Mucopolysaccharidosis type IIID Sanfilippo syndrome | N-Acetylglucosamine 6-sulphatase |
| Mucopolysaccharidosis type IVA Morquio syndrome | Galactose 6-sulphatase |
| Mucopolysaccharidosis type IVB Morquio syndrome | β-Galactosidase |
| Mucopolysaccharidosis type VI | N-Acetylgalactosamine 4-sulphatase |
| Mucopolysaccharidosis type VII Sly syndrome | β-Glucuronidase |
| Mucopolysaccharidosis type IX | hyaluronoglucosaminidase |
| Aspartylglucosaminuria | Aspartylglucosaminidase |
| Cholesterol ester storage disease/Wolman disease | Acid lipase |
| Cystinosis | Cystine transporter |
| Danon disease | Lamp-2 |
| Fabry disease | α-Galactosidase A |
| Farber Lipogranulomatosis/Farber disease | Acid ceramidase |
| Fucosidosis | α-L-Fucosidase |
| Galactosialidosis types I/II | Protective protein |
| Gaucher disease types I/IIIII Gaucher disease | Glucocerebrosidase (β-glucosidase) |
| Globoid cell leucodystrophy/Krabbe disease | Galactocerebrosidase |
| Glycogen storage disease II/Pompe disease | α-Glucosidase |
| GM1-Gangliosidosis types I/II/III | β-Galactosidase |
| GM2-Gangliosidosis type I/Tay Sachs disease | β-Hexosaminidase A |
| GM2-Gangliosidosis type II Sandhoff disease | β-Hexosaminidase A |
| GM2-Gangliosidosis | GM2-activator deficiency |
| α-Mannosidosis types I/II | α-D-Mannosidase |
| β-Mannosidosis | β-D-Mannosidase |
| Metachromatic leucodystrophy | Arylsulphatase A |
| Metachromatic leucodystrophy | Saposin B |
| Mucolipidosis type I/Sialidosis types I/II | Neuraminidase |
| Mucolipidosis types II/III I-cell disease | Phosphotransferase |
| Mucolipidosis type IIIC pseudo-Hurler polydystrophy | Phosphotransferase γ-subunit |
| Multiple sulphatase deficiency | Multiple sulphatases |
| Neuronal Ceroid Lipofuscinosis, CLN1 Batten disease | Palmitoyl protein thioesterase |
| Neuronal Ceroid Lipofuscinosis, CLN2 Batten disease | Tripeptidyl peptidase I |
| Niemann-Pick disease types A/B Niemann-Pick disease | Acid sphingomyelinase |
| Niemann-Pick disease type C1 Niemann-Pick disease | Cholesterol trafficking |
| Niemann-Pick disease type C2 Niemann-Pick disease | Cholesterol trafficking |
| Pycnodysostosis | Cathepsin K |
| Schindler disease types I/II Schindler disease | α-Galactosidase B |
| Sialic acid storage disease | sialic acid transporter |

The melanotransferrin or p97 and the agent are conjugated directly or indirectly to each other (i.e., through an extended linker). The linker can comprise a covalent bond or a peptide of virtually any amino acid sequence or any molecule capable of conjugating melanotransferrin or p97 and the agent. If the linker is a covalent bond or a peptide, then the entire conjugate can be a fusion protein. Such fusion proteins may be produced by recombinant genetic engineering methods known to one of ordinary skill in the art.

The p97-enzyme conjugate according to the invention may be modified as desired to enhance its stability or pharmacokinetic properties (e.g., PEGylation).

III. Compositions and Preparation Thereof

In general, p97-conjugates may be prepared using techniques well known in the art. There are numerous approaches for the conjugation or chemical crosslinking of agents to a polypeptide such as p97, and one skilled in the art can determine which method is most appropriate for conjugating a particular agent. The method employed must be capable of joining the agent with p97 without interfering with the ability of p97 to bind to its receptor, preferably without influencing the biodistribution of the p97-agent compared to p97 alone, and/or without significantly altering the desired activity of the agent (be it therapeutic or prophylactic or the like) once delivered. Preferred methods of conjugating p97 to various agents are described in the examples section, below. A particularly preferred method for linking complex molecules to p97 is the SATA/sulfo-SMCC cross-linking reaction (Pierce (Rockford, Il.)).

Methods of cross linking proteins and peptides are well known to those of skill in the art. Several hundred crosslinkers are available for conjugating a compound of interest with p97 or with a substance which binds p97 (see, e.g., *Chemistry of Protein Conjugation and Crosslinking*, Shans Wong, CRC Press, Ann Arbor (1991) and U.S. Pat. No. 5,981,194 and PCT Patent Publication Nos. WO 02/13843 and WO 01/59459 which are incorporated herein by reference in their entirety). Many reagents and cross-linkers can be used to prepare conjugates of an active agent and a p97 molecule. See, for instance, Hermanson, G T et al. *Bioconjugate Techniques*, Academic Press, (1996). The crosslinker is generally chosen based on the reactive functional groups available or inserted on the therapeutic agent. In addition, if there are no reactive groups, a photoactivatible crosslinker can be used. In certain instances, it may be desirable to include a spacer between p97 and the agent. In one embodiment, p97 and the protein therapeutic agents may be conjugated by the introduction of a sulfhydryl group on p97 and by the introduction of a crosslinker containing a reactive thiol group on to the protein compound through carboxyl groups (Wawizynczak and Thorpe in *Immunoconjugates: Antibody Conjugates in Radioimaging and Therapy of Cancer*, Vogel (Ed.) Oxford University Press, pp. 28-55 (1987); and Blair and Ghose (1983) *J. Immunol. Methods* 59:129). In some embodiments, the linker is vulnerable to hydrolysis at the acidic pH of the lysosome so as to free the agent from the p97 and/or linker.

In some embodiments of the present invention, the p97-agent conjugate is a p97-fusion protein. Fusion proteins may be prepared using standard techniques known in the art. Typically, a DNA molecule encoding p97 or a portion thereof is linked to a DNA molecule encoding the protein compound. The chimeric DNA construct, along with suitable regulatory elements can be cloned into an expression vector and expressed in a suitable host. The resultant fusion proteins contain p97 or a portion thereof used to the selected protein compound.

When a linker is used, the linker is preferably an organic moiety constructed to contain an alkyl, aryl and/or amino acid backbone, and containing an amide, ether, ester, hydrazone, disulphide linkage or any combination thereof. Linkages containing amino acid, ether and amide bound components are stable under conditions of physiological pH, normally 7.4 in serum. Preferred linkages are those containing esters or hydrazones that are stable at serum pH, but that hydrolyze to release the drug when exposed to lysosomal pH. Disulphide linkages are preferred because they are sensitive to reductive cleavage. In addition, amino acid linkers may be designed to be sensitive to cleavage by specific enzymes in the desired target organ or more preferably, the lysosome itself. Exemplary linkers are described in Blattler et al. (1985) *Biochem.* 24:1517-1524; King et al. (1986) *Biochem.* 25:5774-5779; Srinivasachar and Nevill (1989) *Biochem.* 28:2501-2509.

In some embodiments, the linker is a polyethylene glycol or polypropylene glycol. In other embodiments, the linker is from 4 to 20 atoms long. In other embodiments, the linker is from 1 to 30 atoms long with carbon chain atoms which may be substituted by heteroatoms independently selected from the group consisting of O, N, or S. In some embodiments, from 1-4 or from 5 to 15 of the C atoms are substituted with a heteroatom independently selected from O, N, S. In other embodiments, the linker contains a moiety subject to hydrolysis upon delivery to the lysosomal environment (e.g., susceptible to hydrolysis at the lysosomal pH or upon contact to a lysosomal enzyme). In some embodiments, the linker group is preferably hydrophilic to enhance the solubility of the conjugate in body fluids. In some embodiments, the linker contains or is attached to the p97 molecule or the protein agent by a functional group subject to attack by other lysosomal enzymes (e.g., enzymes not deficient in the target lysosome or a lysosomal enzyme not conjugated to the p97 carrier). In some embodiments, the p97 and agent are joined by a linker comprising amino acids or peptides, lipids, or sugar residues. In some embodiments, the p97 and agent are joined at groups introduced synthetically or by posttranslational modifications.

In some embodiments, agent-linker intermediates are similar to what has been described previously, but comprise, for example, either an active ester that can react with free amine groups on p97 or a maleimide that can react with the free thiols created on p97 via a SATA reaction or through other groups where persons skilled in the art can attach them to p97.

A. Preparation of p97

The p97 peptide or molecule for use in the methods and compositions of the present invention may be obtained, isolated or prepared from a variety of sources.

In one aspect, standard recombinant DNA techniques may be used to prepare p97 or derivatives thereof. Within one embodiment, DNA encoding p97 may be obtained by polymerase chain reaction (PCR) amplification of the p97 sequence (see, generally, U.S. Pat. Nos. 4,683,202; 4,683, 195; and 4,800,159; see, also, *PCR Technology: Principles and Applications for DNA Amplification*, Erlich (ed.), Stockton Press (1989)). Briefly, double-stranded DNA from cells which express p97 (e.g., SK-MEL-28 cells) is denatured by heating in the presence of heat stable Taq polymerase, sequence specific DNA primers such as 5' GCGGACTTC-CTCGG 3' (SEQ ID NO:1) and 5' TCGCGAGCTTCCT 3' (SEQ ID NO:2), ATP, CTP, GTP and TTP. Double-stranded DNA is produced when the synthesis is complete. This cycle may be repeated many times, resulting in a factorial amplification of p97 DNA. The amplified p97 DNA may then be readily inserted into an expression vector as described below.

Alternatively, DNA encoding p97 may be isolated using the cloning techniques described by Brown et al. in the UK Patent Application No. GB 2188 637. Clones which contain sequences encoding p97 cDNA have been deposited with the American Type Culture Collection (ATCC) under deposit numbers CRL 8985 (PMTp97b) and CRL 9304 (pSVp97a).

Within one embodiment of the present invention, truncated derivatives of p97 are provided. For example, site-directed mutagenesis may be performed with the oligonucleotide WJ31 5'CTCAGAGGGCCGCTGCGCCC-3'(SEQ ID NO:3) in order to delete the C-terminal hydrophobic domain beyond nucleotide 2219, or with the oligonucleotide WJ32 5' CCA GCG CAG CTAGCGGGGGCAG 3' (SEQ ID NO:4) in order to introduce an Nhe I site and a STOP codon in the region of nucleotides 1146-1166, and thereby also constructing a truncated form of p97 comprising only the N-terminal domain. Similarly, mutagenesis may also be performed on p97 such that only the C-terminal domain is expressed. Within one embodiment, Xho sites are inserted by mutagenesis with the oligonucleotide WJ 5'-ACACCAGCGCAGCTC-GAGGGGCAGCCG 3' (SEQ ID NO:5) into both the N-terminal and C-terminal domains, allowing subsequent deletion of the N-terminal domain. Various other restriction enzymes, including for example, Eco RI, may also be utilized in the context of the present invention in order to construct deletion or truncation derivatives of p97.

Mutations may be introduced at particular loci by synthesizing oligonucleotides containing a mutant sequence, flanked by restriction sites enabling the ligation of the mutated fragments to fragments of the native sequence. Following ligation, the resulting reconstructed sequence encodes a derivative having the desired amino acid insertion, substitution, or deletion. Alternatively, as noted above oligonucleotide-directed site-specific mutagenesis procedures may be employed to obtain an altered gene having particular codons altered according to the desired substitution, deletion, or insertion. Exemplary methods of making the alterations set forth above are disclosed by Sambrook et al. *Molecular Cloning A Laboratory Manual,* 2d Ed., Cold Spring Harbor Laboratory Press (1989).

Within a particularly preferred embodiment of the invention, p97 is cloned into an expression vector as a truncated cDNA with a deletion of the GPI anchor sequence located in the carboxy terminus of the protein.

Briefly, the p97 gene may be generated by polymerase chain reaction (PCR) using the cloned p97 cDNA as a template. The truncated p97 is synthesized using WJ47, the 5' PCR primer encompassing coordinates 36 to 60 (coordinates based on the cDNA map) and additionally containing a Sna BI restriction site. The sequence of WJ47 is 5'-GCG CTA CGT ACT CGA GGC CCC AGC CAG CCC CGA CGG CGC C-3' (SEQ ID NO:6). The 3' primer, WJ48, encompasses coordinates 2172 to 2193 and additionally contains both a TGA termination codon and a SnaBI restriction site. The DNA sequence of WJ48 is 5'-CGC GTA CGT ATG ATC ATC AGC CCG AGC ACT GCT GAG ACG AC-3' (SEQ ID NO:7). Following amplification, the truncated p97 product is inserted into pNUTΔH (obtained from Palmiter (1986) *PNAS* 83:1261-1265) at the Sma I restriction site. The orientations of the resulting plasmids may be determined by PCR using one priming oligonucleotide which anneals to the vector sequence and a second priming oligonucleotide which anneals to the insert sequence. Alternatively, appropriate restriction digests can be performed to verify the orientation. Expression of the amplified sequence results in the production of a soluble p97 protein lacking the hydrophobic domain.

As noted above, the present invention provides recombinant expression vectors which include either synthetic, or cDNA-derived DNA fragments encoding p97 or derivatives thereof, which are operably linked to suitable transcriptional or translational regulatory elements. Suitable regulatory elements may be derived from a variety of sources, including, but not limited to, bacterial, fungal, viral, mammalian, and insect genes. Selection of appropriate regulatory elements is dependent on the host cell chosen, and may be readily accomplished by one of ordinary skill in the art. Examples of regulatory elements include, in particular, a transcriptional promoter and enhancer or RNA polymerase binding sequence, a ribosomal binding sequence, including a translation initiation signal. Additionally, depending on the host cell chosen and the vector employed, other genetic elements, such as an origin of replication, additional DNA restriction sites, enhancers, sequences conferring inducibility of transcription, and selectable markers, may be incorporated into the expression vector.

DNA sequences encoding p97 may be expressed by a wide variety of prokaryotic and eukaryotic host cells, including, but not limited to, bacterial, mammalian, yeast, fungi, viral, plant, and insect cells. Methods for transforming or transfecting such cells for expressing foreign DNA are well known in the art (see, e.g., Itakura et al., U.S. Pat. No. 4,704,362; Hinnen et al. (1978) *PNAS USA* 75:1929-1933; Murray et al., U.S. Pat. No. 4,801,542; Upshall et al., U.S. Pat. No. 4,935,349; Hagen et al., U.S. Pat. No. 4,784,950; Axel et al., U.S. Pat. No. 4,399,216; Goeddel et al., U.S. Pat. No. 4,766,075; and Sambrook et al., supra).

Promoters, terminators, and methods for introducing expression vectors of an appropriate type into, for example, plant, avian, and insect cells may be readily accomplished by those of skill in the art. Within a particularly preferred embodiment of the invention, p97 is expressed from baculoviruses (see, e.g., Luckow and Summers (1988) *BioTechnology* 6:47; Atkinson et al. (1990) *Petic. Sci.* 28:215-224). The use of baculoviruses such as AcMNPV is particularly preferred since host insect cells express the GPI-cleaved forms of p97. p97 may be prepared from cultures of the host/vector systems described above that express the recombinant p97. Recombinantly produced p97 may be further purified as described in more detail below.

The soluble form of p97 may be prepared by culturing cells containing the soluble p97 through the log phase of the cell's growth and collecting the supernatant. Preferably, the supernatant is collected prior to the time at which the cells lose viability. Soluble p97 may then be purified as described below, in order to yield isolated soluble p97. Suitable methods for purifying the soluble p97 can be selected based on the hydrophilic property of the soluble p97. For example, the soluble p97 may be readily obtained by Triton X-114 Phase Separation.

In another embodiment, p97 may be isolated from cultured CHO cells genetically engineered to express the GPI-anchored p97. The GPI-anchored protein may be harvested by a brief incubation with an enzyme capable of cleaving the GPI anchor. Such enzymes are known in the art (Ferguson (1988) *Ann. Rev. Bichem.* 57:285-320) and representative examples are described supra. The cleaved soluble protein may be recovered from the medium, and the cells may then be returned to growth medium for further expression of the protein. Cycles of growth and harvest may be repeated until sufficient quantities of the protein are obtained. A particularly preferred GPI enzyme is phospholipase C (PI-PLC) which may be obtained either from bacterial sources (see, Low "*Phospholipase Purification and Quantification*" The Practical Approach Series: Cumulative Methods Index, Rickwood and Hames, eds. IRC Press, Oxford, N.Y. (1991); Kupe et al. (1989) *Eur. J. Biochem.* 185:151-155; Volwerk et al. (1989) *J. Cell. Biochem.* 39:315-325) or from recombinant sources (Koke et al. (1991) *Protein Expression and Purification* 2:51-58; and Henner et al. (1986) *Nuc. Acids Res.* 16:10383).

p97 and derivatives thereof, including the soluble p97, may be readily purified according to the methods described herein. Briefly, p97 may be purified either from supernatants containing solubilized p97, or from cultured host/vector systems as described above. A variety of purification steps, used either alone or in combination, may be utilized to purify p97. For example, supernatants obtained by solubilizing p97, or from host/vector cultures as described above, may be readily concentrated using commercially available protein concentration filters, such as an Amicon or Millipore Pellicon ultrafiltration unit, or by "salting out" the protein followed by dialysis. In addition, the supernatants or concentrates may be applied to an affinity purification matrix such as an anti-p97 antibody bound to a suitable support. Alternatively, an anion exchange resin, such as a matrix or substrate having pendant diethylaminoethyl (DEAE) groups, may be employed. Representative matrices include acrylamide, agarose, dextran, cellulose or other types commonly employed in protein purification. Similarly, cation exchangers which utilize various insoluble matrices such as sulfopropyl or carboxymethyl groups may be also used.

Finally, one or more reversed-phase high performance liquid chromatography (RP-HPLC) steps using hydrophobic RP-HPLC media, e.g., silica gel having pendant methyl or other alipathic groups, can be employed to further purify p97.

p97 fragments may also be generated using the techniques described above, with modifications well known in the art. For example, p97 expression vectors may be modified so that the expressed protein is a desired fragment of p97. This protein may be isolated from the expression system (i.e., extracted from cells), or it may be designed to be secreted into the supernatant of the expression system, and isolated using techniques described above. Alternatively, full length p97 protein may be generated and purified, and p97 fragments may then be generated by cleavage reactions designed to generate the desired fragment. Chemical synthesis is an alternative route to obtain the desired p97 protein or fragment thereof.

In the context of the present invention, "isolated" or "purified," as used to define the purity of p9'7, refer to a protein that is substantially free of other proteins of natural or endogenous origin, and that contains less than about 5% and preferably less than about 1% by mass of protein contaminants due to the production processes. p97 may be considered "isolated" if it is detectable as a single protein band upon SDS-PAGE, followed by staining with Coomassie Blue.

Production of Fusion/Chimeric Proteins

The chimeric protein of the present invention can be produced using host cells expressing a single nucleic acid encoding the entire fusion protein or more than one nucleic acid sequence, each encoding a domain of the chimeric protein and, optionally, an amino acid or amino acids which will serve to link the domains. The chimeric proteins can also be produced by chemical synthesis.

A. Host Cells

Host cells used to produce chimeric proteins are bacterial, yeast, insect, non-mammalian vertebrate, or mammalian cells; the mammalian cells include, but are not limited to, hamster, monkey, chimpanzee, dog, cat, bovine, porcine, mouse, rat, rabbit, sheep and human cells. The host cells can be immortalized cells (a cell line) or non-immortalized (primary or secondary) cells and can be any of a wide variety of cell types, such as, but not limited to, fibroblasts, keratinocytes, epithelial cells (e.g., mammary epithelial cells, intestinal epithelial cells), ovary cells (e.g., Chinese hamster ovary or CHO cells), endothelial cells, glial cells, neural cells, formed elements of the blood (e.g., lymphocytes, bone marrow cells), muscle cells, hepatocytes and precursors of these somatic cell types.

Cells which contain and express DNA or RNA encoding the chimeric protein are referred to herein as genetically modified cells. Mammalian cells which contain and express DNA or RNA encoding the chimeric protein are referred to as genetically modified mammalian cells. Introduction of the DNA or RNA into cells is by a known transfection method, such as electroporation, microinjection, microprojectile bombardment, calcium phosphate precipitation, modified calcium phosphate precipitation, cationic lipid treatment, photoporation, fusion methodologies, receptor mediated transfer, or polybrene precipitation. Alternatively, the DNA or RNA can be introduced by infection with a viral vector. Methods of producing cells, including mammalian cells, which express DNA or RNA encoding a chimeric protein are described in co-pending patent applications U.S. patent application Ser. No. 08/334,797, entitled "In Vivo Protein Production and Delivery System for Gene Therapy", by Richard F Selden, Douglas A. Treco and Michael W. Heartlein (filed Nov. 4, 1994); U.S. patent application Ser. No. 08/334,455, entitled "In Vivo Production and Delivery of Erythropoietin or Insulinotropin for Gene Therapy", by Richard F Selden, Douglas A. Treco and Michael W. Heartlein (filed Nov. 4, 1994) and U.S. patent application Ser. No. 08/231,439, entitled "Targeted Introduction of DNA Into Primary or Secondary Cells and Their Use for Gene Therapy", by Douglas A. Treco, Michael W. Heartlein and Richard F Selden (filed Apr. 20, 1994). The teachings of each of these applications are expressly incorporated herein by reference.

B. Nucleic Acid Constructs

A nucleic acid construct used to express the chimeric protein can be one which is expressed extrachromosomally (episomally) in the transfected mammalian cell or one which integrates, either randomly or at a pre-selected targeted site through homologous recombination, into the recipient cell's genome. A construct which is expressed extrachromosomally comprises, in addition to chimeric protein-encoding sequences, sequences sufficient for expression of the protein in the cells and, optionally, for replication of the construct. It typically includes a promoter, chimeric protein-encoding DNA and a polyadenylation site. The DNA encoding the chimeric protein is positioned in the construct in such a manner that its expression is under the control of the promoter. Optionally, the construct may contain additional components such as one or more of the following: a splice site, an enhancer sequence, a selectable marker gene under the control of an appropriate promoter, and an amplifiable marker gene under the control of an appropriate promoter.

In those embodiments in which the DNA construct integrates into the cell's genome, it need include only the chimeric protein-encoding nucleic acid sequences. Optionally, it can include a promoter and an enhancer sequence, a polyadenylation site or sites, a splice site or sites, nucleic acid sequences which encode a selectable marker or markers, nucleic acid sequences which encode an amplifiable marker and/or DNA homologous to genomic DNA in the recipient cell to target integration of the DNA to a selected site in the genome (targeting DNA or DNA sequences).

C. Cell Culture Methods

Mammalian cells containing the chimeric protein-encoding DNA or RNA are cultured under conditions appropriate for growth of the cells and expression of the DNA or RNA. Those cells which express the chimeric protein can be identified, using known methods and methods described herein, and the chimeric protein isolated and purified, using known methods and methods also described herein; either with or without amplification of chimeric protein production. Identification can be carried out, for example, through screening genetically modified mammalian cells displaying a phenotype indicative of the presence of DNA or RNA encoding the chimeric protein, such as PCR screening, screening by Southern blot analysis, or screening for the expression of the chimeric protein. Selection of cells having incorporated chimeric protein-encoding DNA may be accomplished by including a selectable marker in the DNA construct and culturing transfected or infected cells containing a selectable marker gene under conditions appropriate for survival of only those cells which express the selectable marker gene. Further amplification of the introduced DNA construct can be effected by culturing genetically modified mammalian cells under conditions appropriate for amplification (e.g., culturing genetically modified mammalian cells containing an amplifiable marker gene in the presence of a concentration of a drug at which only cells containing multiple copies of the amplifiable marker gene can survive). Genetically modified mammalian cells expressing the chimeric protein can be identified, as described herein, by detection of the expression product. For example, mammalian cells expressing chimeric protein in which the carrier is p97 can be identified by a sandwich enzyme immunoassay. The antibodies can be directed toward the LRP portion or the active agent portion.

B. Preparation of Antibodies to p97

Based on the teaching of the instant specification, antibodies to mouse or human p97 have many uses including, but not limited to, the use for the isolation and purification of p97, use in research and identification of p97 both in vitro and in vivo, and potential diagnostic (e.g., monitoring conjugate dosage levels) and therapeutic uses (e.g., modulating p97-conjugate dose levels). It is, therefore, useful to briefly set forth preferred antibodies to p97, and methods of producing such antibodies.

Antibodies reactive against p97 are well known in the art. Additional anti-p97 antibodies are provided by the present invention. Representative examples of anti-p97 antibodies include L235 (ATCC No. HB 8466; see, Real et al. (1985) *Cancer Res.* 45:4401 4411; see, also, Food et al. (1994) *J. Biol. Chem.* 269(4): 3034-3040), 4.1, 8.2, 96.5 and 118.1 (see, Brown et al. (1981) *J. Immunol.* 127(2):539-546; and Brown et al. (1981) *Proc. Natl. Acad. Sci. USA* 78(1):539-543); and HybC (Kennard et al. (1996) *Nat. Med.* 2(11):1230-1235). Other monoclonal antibodies, including, but not limited to, 2C7 and 9B6, have been generated at Synapse Technologies Inc. Antibodies to the mouse p97 include, for example, a rabbit anti-human p97 polyclonal antibody generated against a fragment of the mouse p97. In the context of the present invention, antibodies are understood to include, for example, monoclonal antibodies, polyclonal antibodies, antibody fragments (e.g., Fab, and F(ab')$_2$) and recombinantly produced binding partners. Antibodies are understood to be reactive against p97 if the Ka is greater than or equal to $10^{-7}$ M.

Polyclonal antibodies may be readily generated by one of ordinary skill in the art from a variety of warm-blooded animals. Monoclonal antibodies may also be readily generated using conventional techniques (see, e.g., U.S. Pat. Nos. RE 32,011, 4,902,614; 4,543,439; and 4,411,993; see, also, Kennett, McKearn, and Bechtol (eds.) *Monoclonal Antibodies, Hybridomas: A New Dimension in Biological Analyses*, Plenum Press, (1980); and Harlow and Lane (eds.) *Antibodies: A Laboratory Manual*, Cold Spring Harbor Laboratory Press (1988)). Preparation of preferred antibodies is further described in the examples section, below.

Labels

In some embodiments, the p97 conjugate is labeled to facilitate its detection. A "label" or a "detectable moiety" is a composition detectable by spectroscopic, photochemical, biochemical, immunochemical, chemical, or other physical means. For example, labels suitable for use in the present invention include, for example, radioactive labels (e.g., $^{32}$P), fluorophores (e.g., fluorescein), electron-dense reagents, enzymes (e.g., as commonly used in an ELISA), biotin, digoxigenin, or haptens and proteins which can be made detectable, e.g., by incorporating a radiolabel into the hapten or peptide, or used to detect antibodies specifically reactive with the hapten or peptide.

As noted above, depending on the screening assay employed, the agent, the linker or the p97 molecule portion of a conjugate may be labeled. The particular label or detectable group used is not a critical aspect of the invention, as long as it does not significantly interfere with the biological activity of the conjugate. The detectable group can be any material having a detectable physical or chemical property. Thus, a label is any composition detectable by spectroscopic, photochemical, biochemical, immunochemical, electrical, optical or chemical means.

Examples of labels suitable for use in the present invention include, but are not limited to, fluorescent dyes (e.g., fluorescein isothiocyanate, Texas red, rhodamine, and the like), radiolabels (e.g., $^3$H, $^{125}$I, $^{35}$S, $^{14}$C, or $^{32}$P), enzymes (e.g., horse radish peroxidase, alkaline phosphatase and others commonly used in an ELISA), and colorimetric labels such as colloidal gold or colored glass or plastic beads (e.g., polystyrene, polypropylene, latex, etc.).

The label may be coupled directly or indirectly to the desired component of the assay according to methods well known in the art. Preferably, the label in one embodiment is covalently bound to p97 using an isocyanate reagent for conjugating an active agent according to the invention. In one aspect of the invention, the bifunctional isocyanate reagents of the invention can be used to conjugate a label to p97 to form a label p97 conjugate without an active agent attached thereto. The label p97 conjugate may be used as an intermediate for the synthesis of a labeled conjugate according to the invention or may be used to detect the p97 conjugate. As indicated above, a wide variety of labels can be used, with the choice of label depending on sensitivity required, ease of conjugation with the desired component of the assay, stability requirements, available instrumentation, and disposal provisions. Non-radioactive labels are often attached by indirect means. Generally, a ligand molecule (e.g., biotin) is covalently bound to the molecule. The ligand then binds to another molecules (e.g., streptavidin) molecule, which is either inherently detectable or covalently bound to a signal system, such as a detectable enzyme, a fluorescent compound, or a chemiluminescent compound.

The conjugates can also be conjugated directly to signal generating compounds, e.g., by conjugation with an enzyme or fluorophore. Enzymes suitable for use as labels include, but are not limited to, hydrolases, particularly phosphatases, esterases and glycosidases, or oxidotases, particularly peroxidases. Fluorescent compounds, i.e., fluorophores, suitable for use as labels include, but are not limited to, fluorescein and its derivatives, rhodamine and its derivatives, dansyl, umbelliferone, etc. Further examples of suitable fluorophores include, but are not limited to, eosin, TRITC-amine, quinine, fluorescein W, acridine yellow, lissamine rhodamine, B sulfonyl chloride erythroscein, ruthenium (tris, bipyridinium), Texas Red, nicotinamide adenine dinucleotide, flavin adenine dinucleotide, etc. Chemiluminescent compounds suitable for use as labels include, but are not limited to, luciferin and 2,3-dihydrophthalazinediones, e.g., luminol. For a review of various labeling or signal producing systems that can be used in the methods of the present invention, see U.S. Pat. No. 4,391,904.

Means of detecting labels are well known to those of skill in the art. Thus, for example, where the label is a radioactive label, means for detection include a scintillation counter or photographic film as in autoradiography. Where the label is a fluorescent label, it may be detected by exciting the fluorochrome with the appropriate wavelength of light and detecting the resulting fluorescence. The fluorescence may be detected visually, by the use of electronic detectors such as charge coupled devices (CCDs) or photomultipliers and the like. Similarly, enzymatic labels may be detected by providing the appropriate substrates for the enzyme and detecting the resulting reaction product. Colorimetric or chemiluminescent labels may be detected simply by observing the color associated with the label. Other labeling and detection systems suitable for use in the methods of the present invention will be readily apparent to those of skill in the art. Such labeled modulators and ligands may be used in the diagnosis of a disease or health condition.

Pharmaceutical Compositions, and Methods of Use/Treatment/Administration

The diseases that can be treated, ameliorated or prevented using the methods of the present invention include, but are not limited to the following: Mucopolysaccharidosis I (MPS I), MPS II, MPS IIIA, MPS UM, Metachromatic Leukodystropy (MLD), Krabbe, Pompe, CLN2, Tay-Sachs, Niemann-Pick A and B, and other lysosomal diseases. For each disease the conjugated agent would comprise a specific compound, protein or enzyme. For methods involving MPS I, the preferred compound or enzyme is α-L-iduronidase. For methods involving MPS II, the preferred compound or enzyme iduronate-2-sulfatase. For methods involving MPS IIIA, the preferred compound or enzyme is heparan N-sulfatase. For methods involving MPS IIIB, the preferred compound or enzyme is α-N-acetylglucosaminidase. For methods involving Metachromatic Leukodystropy (MLD), the preferred compound or enzyme is Arylsulfatase A. For methods involving Krabbe, the preferred compound or enzyme is Galactosylceramidase. For methods involving Pompe, the preferred compound or enzyme is acid-alpha-glucosidase. For methods involving CLN, the preferred compound or enzyme is thioesterase. For methods involving Tay-Sachs, the preferred compound or enzyme is hexosaminidase A. For methods involving Niemann-Pick A and B the preferred compound or enzyme is Acid Spingomyelinase. For methods involving other Glycogenosis disorders the preferred compound or enzyme is glycolipidoses, mucopolysaccharidoses, oligosaccharidoses.

The p97-conjugates of the present invention can be administered with a "pharmaceutically acceptable carrier." Such carriers encompass any of the standard pharmaceutical carriers, buffers and excipients, including phosphate-buffered saline solution, water, and emulsions (such as an oil/water or water/oil emulsion), and various types of wetting agents and/or adjuvants. Suitable pharmaceutical carriers and their formulations are described in Remington's Pharmaceutical Sciences (Mack Publishing Co., Easton, 19th ed. 1995). Preferred pharmaceutical carriers depend upon the intended mode of administration of the active agent. Typical modes of administration are described below.

The term "effective amount" means a dosage sufficient to produce a desired result on a health condition, pathology, disease of a subject or for a diagnostic purpose. The desired result may comprise a subjective or objective improvement in the recipient of the dosage.

A "prophylactic treatment" is a treatment administered to a subject who does not exhibit signs of a disease or exhibits only early signs of a disease, wherein treatment is administered for the purpose of decreasing the risk of developing a pathology. The conjugate conjugates of the invention may be given as a prophylactic treatment.

A "therapeutic treatment" is a treatment administered to a subject who exhibits signs of pathology, wherein treatment is administered for the purpose of diminishing or eliminating those pathological signs. The signs may be subjective or objective.

The term "composition", as in pharmaceutical composition, is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a p97-agent conjugate of the present invention and a pharmaceutically acceptable carrier.

The term "pharmaceutical composition" indicates a composition suitable for pharmaceutical use in a subject, including an animal or human. A pharmaceutical composition generally comprises an effective amount of the p97-conjugate and a pharmaceutically acceptable carrier.

The conjugates may be administered by a variety of routes. For oral preparations, the conjugates can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

The p97-agent conjugates can be formulated into preparations for injection by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

The p97-agent conjugates can be utilized in aerosol formulation to be administered via inhalation. The conjugates of the present invention can be formulated into pressurized acceptable propellants such as dichlorodifluoromethane, propane, nitrogen and the like.

Furthermore, the p97-agent conjugates can be made into suppositories by mixing, with a variety of bases such as emulsifying bases or water-soluble bases. The conjugates of the present invention can be administered rectally via a suppository. The suppository can include vehicles such as cocoa butter, carbowaxes and polyethylene glycols, which melt at body temperature, yet are solidified at room temperature.

Unit dosage forms of the p97-agent conjugates for oral or rectal administration as, for instance, syrups, elixirs, and suspensions may be provided wherein each dosage unit, for example, teaspoonful, tablespoonful, tablet or suppository, contains a predetermined amount of the composition containing active agent. Similarly, unit dosage forms for injection or intravenous administration may comprise the conjugate in a composition as a solution in sterile water, normal saline or another pharmaceutically acceptable carrier. The term "unit dosage form," as used herein, refers to physically discrete units suitable as unitary dosages for human and animal subjects, each unit containing a predetermined quantity of conjugates of the present invention calculated in an amount sufficient to produce the desired effect in association with a pharmaceutically acceptable diluent, carrier or vehicle. The specifications for the novel unit dosage forms of the present invention depend on the particular conjugate employed and the effect to be achieved, and the pharmacodynamics associated with each compound in the host.

In practical use, the conjugates according to the invention can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). In preparing the compositions for oral dosage form, any of the usual pharmaceutical media may be employed, such as, for example, water, glycols, oils, alcohols, flavoring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations such as, for example, powders, hard and soft capsules and tablets, with the solid oral preparations being preferred over the liquid preparations.

With respect to transdermal routes of administration, methods for transdermal administration of drugs are disclosed in Remington's Pharmaceutical Sciences, 17th Edition, (Gennaro et al. Eds., Mack Publishing Co., 1985). Dermal or skin patches are a preferred means for transdermal delivery of the p97-agent conjugates of the invention. Patches preferably provide an absorption enhancer such as DMSO to increase the absorption of the conjugates. Other methods for transdermal drug delivery are disclosed in U.S. Pat. Nos. 5,962,012, 6,261,595, and 6,261,595. Each of which is incorporated by reference in its entirety.

The pharmaceutically acceptable excipients, such as vehicles, adjuvants, carriers or diluents, are commercially available. Moreover, pharmaceutically acceptable auxiliary substances, such as pH adjusting and buffering agents, tonicity adjusting agents, stabilizers, wetting agents and the like, are commercially available.

Those of skill will readily appreciate that dose levels can vary as a function of the specific agent, the severity of the symptoms and the susceptibility of the subject to side effects. Preferred dosages for a given conjugate are readily determinable by those of skill in the art by a variety of means.

In each of these aspects, the compositions include, but are not limited to, compositions suitable for oral, rectal, topical, parenteral (including subcutaneous, intramuscular, and intravenous), pulmonary (nasal or buccal inhalation), or nasal administration, although the most suitable route in any given case will depend in part on the nature and severity of the conditions being treated and on the nature of the active ingredient. Exemplary routes of administration are the oral and intravenous routes. The compositions may be conveniently presented in unit dosage form and prepared by any of the methods well-known in the art of pharmacy.

In practical use, the conjugates according to the invention can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). In preparing the compositions for oral dosage form, any of the usual pharmaceutical media may be employed, such as, for example, water, glycols, oils, alcohols, flavoring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations such as, for example, powders, hard and soft capsules and tablets, with the solid oral preparations being preferred over the liquid preparations.

Because of their ease of administration, tablets and capsules represent the most advantageous oral dosage unit form in which case solid pharmaceutical carriers are obviously employed. If desired, tablets may be coated by standard aqueous or nonaqueous techniques. The percentage of an active agent in these compositions may, of course, be varied and may conveniently be between about 2 percent to about 60 percent of the weight of the unit.

The conjugates of the invention are useful for therapeutic, prophylactic and diagnostic intervention in animals, and in particular in humans.

Compositions of the present invention may be administered encapsulated in or attached to viral envelopes or vesicles. Liposomes are vesicles formed from a bilayer membrane. Suitable vesicles include, but are not limited to, unilamellar vesicles and multilamellar lipid vesicles or liposomes. Such vesicles and liposomes may be made from a wide range of lipid or phospholipid compounds, such as phosphatidylcholine, phosphatidic acid, phosphatidylserine, phosphatidylethanolamine, sphingomyelin, glycolipids, gangliosides, etc. using standard techniques, such as those described in, e.g., U.S. Pat. No. 4,394,448. Such vesicles or liposomes may be used to administer conjugates intracellularly and to deliver the conjugates to the target organs. Controlled release of a p97-composition of interest may also be achieved using encapsulation (see, e.g., U.S. Pat. No. 5,186,941).

Any route of administration which brings the conjugates into contact with the target cells, tissue or organ may be used. The conjugates can be administered peripherally or centrally. The conjugates may also be administered intravenously or by intraperitoneally. The conjugates may be administered locally or regionally.

The dosages to be administered will depend on individual needs and characteristics (age, weight, severity of condition, on the desired effect, the active agent used, and the chosen route of administration and treatment regimen). Preferred dosages of p97-conjugates range from about 0.02 pmol/kg to about 2.5 nmol/kg, and particularly preferred dosages range from 2-250 pmol/kg; alternatively, preferred doses of the p97 conjugate may be in the range of 0.02 to 2000 mg/kg. These dosages will be influenced by the number of agent moieties associated with each p97 molecule. In addition, dosages may be calculated based on the agent to be administered and the severity of the condition to be treated. Empirical and theoretical methods for determining dose response relationships and optimizing the dosages employed an individual patients therapy are will known to one of ordinary skill in the art.

The p97-conjugates of the invention are, for example, useful for therapeutic and prophylactic intervention the treatment of lysosomal storage diseases in animals, and in particular in humans. The subject methods find use in the treatment of a variety of different lysosomal storage diseases. In certain embodiments, of particular interest is the use of the subject methods in disease conditions where an active agent having desired activity has been previously identified, but in which the active agent is not adequately targeted to the target site, area or compartment. With such active agent, the subject methods can be used to enhance the therapeutic efficacy and therapeutic index of active agent.

Treatment is meant to encompass any beneficial outcome to a subject associated with administration of a conjugate including a reduced likelihood of acquiring a disease, prevention of a disease, slowing, stopping or reversing, the progression of a disease or an amelioration of the symptoms associated with the disease condition afflicting the host, where amelioration or benefit is used in a broad sense to refer to at least a reduction in the severity of the disease or in a magnitude of a parameter representative of the severity or presence of the disease, e.g., tissue damage, cell death, excess or harmful amounts of lysosomal storage materials, symptoms, associated with the pathological condition being treated, such as inflammation and pain associated therewith. As such, treatment also includes, but is not limited to, situations where the pathological condition, or at least symptoms associated therewith, are completely inhibited, e.g., prevented from happening, or stopped, e.g., terminated, such that the host no longer suffers from the pathological condition, or at least the symptoms that characterize the pathological condition.

A variety of hosts or subjects are treatable according to the subject methods. Generally such subjects are "mammals" or "mammalian," where these terms are used broadly to describe organisms which are within the class mammalia, including the orders carnivore (e.g., dogs and cats), rodentia (e.g., mice, guinea pigs, and rats), and primates (e.g., humans, chimpanzees, and monkeys). In many embodiments, the hosts or subjects will be humans.

Methods of Screening Conjugates for Therapeutic Activity

The ability of the conjugates of the present invention to increase the delivery of a therapeutic agent to a lysosome can be assessed in vitro by comparing the delivery of a p97 conjugated agent to a control such as the unconjugated agent. In a preferred embodiment, the conjugate and agent are administered in vitro to cells and the localization of the conjugate within lysosomes determined. The assessment is facilitated by conjugating a label to the p97 conjugate or unconjugated agent so that its location within the cell can be more easily determined and quantified. Methods for monitoring the localization of compounds within a cell are well known to one of ordinary skill in the art and further exemplified in Examples 1 and 2. Such methods are also exemplified in U.S. patent application Ser. No. 10/206,448 filed on Jul. 25, 2002 and incorporated herein by reference in its entirety.

In another functional approach, the conjugate with an agent deficient in a LSD can be contacted in vitro with cells affected by the LSD and the effect of the conjugate on the amount of the storage material found within the lysosomes compared to the effect of an equivalent amount of the unconjugated agent. The cell or lysosomal volumes may be measured or the stored material directly quantitated.

In some embodiments, the invention provides a method of screening a compound for therapeutic activity in treating a lysosomal storage disease, by contacting a cell having a lysosome with the compound, wherein the compound comprises p97 covalently linked to an enzyme deficient in a lysosomal storage disease; and then monitoring delivery of the compound to the lysosome. The monitoring may be by means of a label on the conjugate and detecting the label within the lysosome or by determining the effect of the compound on the lysosomal storage material (e.g., does it reduce the amount of storage material.) In some embodiments, the cell is human.

In a further method, clinical trials are conducted as known to one of ordinary skill in the art and has exemplified in Example 3. More preferably, the conjugates are administered to test animals providing an animal model of the LSD of interest. Such animal models are well known to one of ordinary skill in the art. See, for example, PCT Patent Publication No: WO 01/83722 which is incorporated herein by reference.

The following examples further illustrate the present invention. These examples are intended merely to be illustrative of the present invention and are not to be constructed as being limiting.

EXAMPLES

Example 1

Immunocytochemical Localization of p97

The focus of our first set of experiments has been to show that unconjugated p97 is localized to the lysosome in cultured brain cells. This is accomplished by showing "co-localization" of p97 with a marker for lysosomes within the cell. Showing lysosomal "co-localization" is the first step toward validating p97 as a suitable vehicle for lysosomal enzymes.

A human neuronal line was used to conduct initial experiments. Differentiated human NT2 neurons derived from a teratocarcinoma are available commercially from Stratagene. Human neuronal lines are the most relevant system since the p97 protein under study is of human origin and the ultimate target is the neural tissue within affected patients.

Immunocytochemical staining of p97 within cells was accomplished with the L235 monoclonal antibody from Synapse in conjunction with a fluorescein-conjugated secondary antibody to localize the L235. The anti-p97 L235 antibody detects endogenous material (p97 is expressed in normal neuronal cells) in addition to material that has been taken up from the culture medium. Markers are necessary to provide an organelle-specific fluorescence pattern against which the observed p97 fluorescence pattern can be compared. Overlap of the two patterns confirms the specific intracellular localization of p97. For this purpose, an antibody against Cathepsin L, a lysosomal protease, was used in combination with L235 in the immunofluorescence experiments. This anti-Cathepsin L antibody was raised against a C-terminal peptide of murine Cathepsin L and shows strong staining of lysosomes in human neuronal cells. A Texas red-conjugated secondary antibody was used to detect the anti-Cathepsin L primary antibody. Human NT2 neurons were grown on glass cover slips and fed for 2 hours with 0.5 mg/ml p97. Cells were then rinsed, fixed with formaldehyde and permeabilized. Fixed cells were co-stained with primary and secondary antibodies and mounted on slides. Cells were also treated with a stain for the nucleus, DAPI. Slides were imaged using appropriate filter sets to resolve the different markers.

Experimental Methods

Cell type: Human neuronal cell lines were primarily used to conduct these experiments. Differentiated human NT2 neurons derived from a teratocarcinoma are available commercially from Stratagene. CRL10742 and CRL10442 immature cortical neurons are available from ATCC. CRL10742 (designation HCN-2) was developed from a patient with Rasmussen's encephalitis and stains for neuronal markers but not for non-neuronal markers. This cell line is covered by U.S. Pat. No. 5,196,315 for use in screening methods for evaluation of chemical and biological compounds. CRL10442 (designation HCN-1A) is a brain cortical neuron derived from a patient suffering unilateral megalencephaly. Human neuronal lines are the most relevant system to the current investigations as the p97 protein under study is of human origin and the ultimate target is the neuronal tissue within affected patients. Fibroblasts from MPSI patient were obtained from BioMarin stock of this cell line originally obtained from the Coriell Cell Bank. Cells were maintained in DMEM with 10% Fetal Bovine Serum (FBS).

Antibodies: The mouse anti-p97 monoclonal antibody L235 was kindly provided by Synapse. An appropriate dilution for immunohistochemistry was determined by titration of antibody against fixed DG44 cells until no background signal was visible. Rabbit anti-Cathepsin L (M–19) antibody was purchased from Santa Cruz Biotech. Secondary antibodies, Donkey anti-Mouse (DAM) and Goat Anti-Rabbit (GAR) conjugated with Alexa Fluor 488 or Alexa Fluor 594 were purchased from Molecular Probes and used at dilutions recommended by the manufacturer.

Fluorescent Probes: Molecular Probes Alexa Fluor protein labeling kits were used to fluorescently tag p97 and Iduronidase. Fluorescently labeled Transferrin is commercially available from Molecular Probes. Lysosensor is a marker for acidic organelles commercially available from Molecular Probes.

Equipment: Examination of fixed cells was carried out using a Leica DMIRB with the following filter sets: Leica Filter Cube A (UV excitation range) Excitation Filter BP340-380/Emission LP425. Leica Filter Cube 13 (Blue excitation range) Excitation Filter BP450-490/Emission LP515, used to visualize the Alexa Fluor 488 tag. Leica Filter Cube N2.1, (Green excitation range) Excitation Filter BP515-560/Emission LP590, used to visualize the Alexa Fluor 594 tag.

Protein Uptake Conditions: Cells were seeded a day prior to an uptake experiment on coverslips within six-well plates at a density of between 2 and 5e5 cells per well. Cells were washed 3 times with serum-free DMEM+1 mg/ml BSA. Proteins for uptake were added to the cells at 60 ug/ml in DMEM+1 mg/ml BSA and incubated in a 37° C. incubator with 5% $CO_2$ for the duration of the uptake period. Cells were then washed 3 times with PBS and fixed with a commercially available formaldehyde-based fixative available from CALTAG. Cells were permeabilized by immersion in 70% ethanol. Antibody staining was carried out in CALTAG permeabilization solution. All steps were separated by 3 washes in PBS the first of which contained 0.1 ug/ml DAPI to stain cell nuclei. Coverslips were mounted in Molecular Probes Antifade for examination.

Results

The immunofluorescence images depicted in FIG. 1A-1D show the results of a co-localization experiment in human NT2 neurons using the L235 and anti Cathepsin L antibodies. The "Light Microscopy" frame of FIG. 1A shows a single cultured human neuron observed under phase-contrast with additional irradiation at the excitation wavelength of DAPI. The nucleus, which is indicated by the blue fluorescent signal, is located in the center of the frame. The cytoplasm of this cell can be seen streaming away from the nucleus.

The "Cathepsin Staining" frame (FIG. 1B) is the same cell viewed under irradiation with light at the excitation wavelength for Cathepsin L detection. The location of Cathepsin L is identified by the red fluorescence. The punctate appearance of the signal pattern seen in this frame is characteristic of lysosomes.

The "L235 Staining" frame of (FIG. 1C) is of the same cell but now irradiated with light at the excitation wavelength for p97 detection. The location of p97 is identified by green fluorescence. This frame shows the same type of punctate lysosomal staining pattern as can be seen in the Cathepsin L image. Careful comparison of the fluorescent patterns in these two frames reveals that they are coincident. The Cathepsin L and the p97 are localized identically within the cell.

Confirmation of the co-localization of the p97 and Cathepsin L is shown in FIG. 1D ("Overlay"). Combining the two fluorescent signals yields a orange colored punctate pattern, a combination of the red and green light from the two different antibodies. These results have been replicated in the ATCC neuronal line CRL 10742 that is derived from human brain cortical tissue.

Example 2

Intracellular Fluorescence Detection of Tagged p97

Selective tracking of endocytosed material within a background of endogenous material requires the use of a second detection system. For this purpose, cells were fed with p97, which had been conjugated to the fluorescent marker Alexa Fluor 594. Observation of marker fluorescence from live cells permits identification of the signal derived solely from endocytosed p97 with no contribution from endogenous material. A lysosomal marker for live cells was necessary for co-localization with the Alexa Fluor 594 tagged p97. Such a marker is Lysosensor Green, a dye taken up by living cells that becomes fluorescent upon exposure to the acidic environment of the late-endosomal and lysosomal compartments. Similar to the experiment outlined above, cells were fed for 2 hours with 0.5-mg/ml p97 and washed to remove unbound material and live cells were imaged using appropriate filter sets to resolve the different markers.

Experimental Methods

See "Experimental Methods" of Example 1.

Results

The localization of endocytosed Alexa Fluor 594-p97 was determined in live cells. Cells were observed directly on a fluorescence microscope using appropriate filter sets.

Selective tracking of endocytosed material within a background of endogenous material requires the use of a second detection system. For this purpose, cells were fed with p97 conjugated to the fluorescent marker Alexa Fluor 594. Observation of marker fluorescence from live cells permits identification of the signal derived solely from endocytosed p97 with no contribution from endogenous material. A lysosomal marker for live cells was necessary for co-localization with the Alexa Fluor 594 tagged p97. Such a marker is Lysosensor Green, a dye taken up by living cells that becomes fluorescent upon exposure to the acidic environment of the late endosomal and lysosomal compartments. Similar to the experiment outlined above, cells were fed for 2 hours with 0.5 mg/ml p97 and washed to remove unbound material and live cells were imaged using appropriate filter sets to resolve the different markers.

Figure 2:
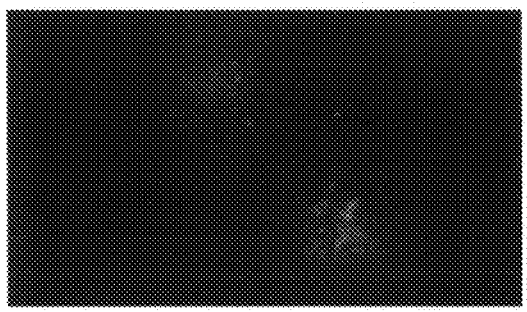
FIGS. 2A-2C depict live neurons fed with AlexaFluor 594-p97 and lysosensor green (see, Example 2 for details).
Figure 2:
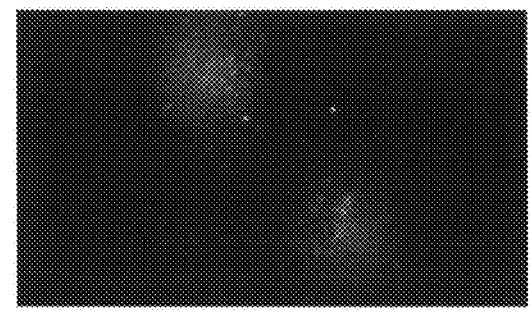
Figure 2:
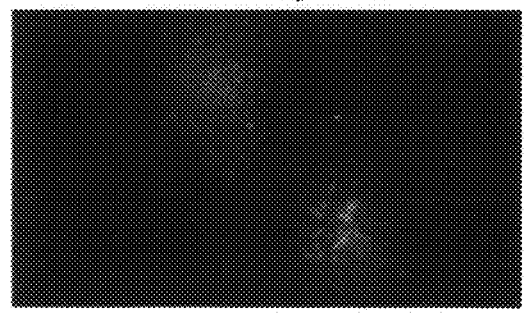

The localization of endocytosed Alexa Fluor 594-p97 was determined in live cells. Cells were observed directly on a fluorescence microscope using appropriate filter sets (FIG. 2A-2C). The "Alexa Fluor 594-p97" frame (FIG. 2A) shows a living hNT neuronal cell fed with the fluorophore-tagged p97 and Lysosensor Green. The cell in this frame is observed under irradiation at the excitation wavelength of Alexa Fluor 594. The location of the endocytosed p97 is identified by the red fluorescence. The pattern is punctate and perinuclear. The "Lysosensor Green" frame (FIG. 2B) is the same cell viewed under irradiation with light at the excitation wavelength of Lysosensor Green. The locations of the acidified compartments of the cell, including the lysosomes and late-endosomes, are identified by green fluorescence. This pattern is also punctate and perinuclear. Co-localization of the endocytosed p97 and Lysosensor dye is shown in the third frame ("Overlay") (FIG. 2C). Combining the two fluorescent signals yields an orange-colored pattern, a combination of the red and green light from the two different fluorescent markers.

The above-experimental data (Examples 1-2) shows that p97 is localized in the lysosomes and transported from the cell surface to the lysosomes of cultured cells. The two main transport steps required for p97-mediated delivery to brain cell lysosomes seem to occur. Synapse has shown that the p97 molecule delivers its "payload" across the BBB. Our results have shown that p97 is transported to the lysosome in cultured brain cells. Taken together these results indicate that p97 is an effective means to deliver recombinant enzymes to LSD patients suffering from neurological manifestations of the disease.

Example 3

Treatment of Patients with MPS-I Disorder

A pharmaceutical composition comprising a conjugated agent comprising human α-L-iduronidase linked to p97 is prepared by methods well-known to one skilled in the art. It is preferred to administer the pharmaceutical composition intravenously. The final dosage form of the fluid comprises the conjugated agent, normal saline, phosphate buffer at pH 5.8 and human albumin at 1 mg/ml. These are prepared in a bag of normal saline.

| Component | Composition |
|---|---|
| Conjugated agent (α-L-iduronidase linked to p97) | 0.05 0.5 mg/mL or 12,500-50,000 units per mL |
| Sodium chloride solution | 150 mM in an IV bag, 50-250 cc total volume |
| Sodium phosphate buffer | 10-50 mM, pH 5.8 |
| Human albumin | 1 mg/mL |

Human patients manifesting a clinical phenotype of MPS-I disorder with an α-L-iduronidase level of less than 1% of normal in leukocytes and fibroblasts are included in the study. All patients manifest some clinical evidence of visceral and soft tissue accumulation of glycosaminoglycans with varying degrees of functional impairment. Efficacy is determined by measuring the percentage reduction in urinary GAG excretion over time. The urinary GAG levels in MPS-I patients are compared to normal excretion values. There is a wide range of urine GAG values in untreated MPS-I patients. A greater than 50% reduction in excretion of undegraded GAGs following therapy with the conjugated agent is a valid means to measure an individual's response to therapy. Data is collected measuring the leukocyte iduronidase activity and buccal iduronidase activity before and after therapy in MPS-I patients. Clinical assessment of liver and spleen size is performed as it is the most widely accepted means for evaluating successful bone marrow transplant treatment in MPS-I patients (Hoogerbrugge et al., Lancet 345:1398 (1995)).

Example 4

Methods and Compositions Linking Agents to the p97 Molecule

Conjugates and preferred embodiments according to the present invention include those of the formula Formula I 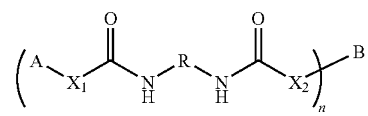 in which A is an active agent and B is a p97 molecule for targeting or delivery; and $X_1$ and $X_2$ are independently N or O; R is a substituted alkyl or unsubstituted alkyl or unsubstituted or substituted heteroalkyl from 1 to about 30 atoms in length or 1 to 50 atoms in length; and n is from 1 to 30. Where n is greater than 1, the active agents may be the same or different. Where different, the active agents are useful for the treatment of the same disease or condition. "Alkyl" encompasses divalent radicals of alkanes as defined below. Such linkers are taught in U.S. Provisional Application No. 60/395,762 filed on Jul. 12, 2002 and incorporated herein by reference in its entirety.

In a further embodiment, a label, L, is covalently attached to a compound of Formula I. The label may be attached to the conjugate at the active agent portion, the p97 portion, or the linker joining the active agent to p97:

Formula V

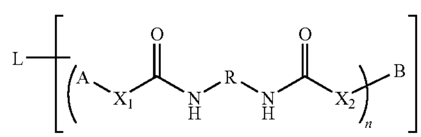

In some embodiments, the label is preferably attached to the p97 portion of a conjugate.

These conjugates have the advantage of release ability. When an isocyanate reagent according to the invention reacts with a hydroxy group it forms a carbamate bond, which can be hydrolyzed by endogenous enzymes (e.g., proteases) in the body of a subject to which it is administered. The isocyanate reagents according to the invention react with an amino group to generate an isourea bond, which can also be hydrolyzed by endogenous enzymes in the body of a subject to which it is administered. By virtue of attachment to the p97 moeity, the agent is delivered to the target lysosomal compartment or site in the body, the protease or other endogenous enzyme hydrolyzes the carbamate or isourea bond to release the free drug at the target site or compartment.

An exemplary conjugate comprises a p97 covalently linked through functional group, as is well known in the art of PEGylated peptides and proteins to a PEG moiety which is in turned linked via a carbamate linkage to the active agent. The term active agent includes, but is not limited to, proteins or enzymes deficient in a LSD. In another embodiment, the conjugate is covalently linked through a carbamate group to a PEG moiety which is in turned linked via a carbamate linkage to the active agent. In another embodiment, the conjugate is covalently linked through a carbamate group to a PEG moiety which is in turned linked via a carbamate linkage to an alkyl or homoalkyl moiety which is in turned linked via a carbamate linkage to the active agent.

These conjugates also have the advantage of being synthesized with high efficiencies according to the inventive methods. The inventive reactions between isocyanate groups with hydroxy and amino are very efficient; and the yields are very high (usually over 90%). In addition, the new bond formed by the reaction of an isocyanate group with a hydroxy or an amino group will increase aqueous solubility of the drug. This property can be of practical importance.

Example 5

Treatment of Patients with a Lysosomal Storage Disease Disorder

A pharmaceutical composition comprising a conjugated agent comprising a human enzyme or protein deficient in a lysosomal storage disease linked to p97 is prepared by methods well-known to one skilled in the art. It is preferred to administer the pharmaceutical composition intravenously. Alternatively, the composition can be administered locally to the affected organ(s). The final dosage form of the fluid comprises the conjugated agent, normal saline, phosphate buffer at pH 5.8 and human albumin at 1 mg/ml. These are prepared in a bag of normal saline.

| Component | Composition |
|---|---|
| Conjugated agent (lysosomal storage disease protein or enzyme linked to p97) | 0.02 to 2.0 mg/mL |
| Sodium chloride solution | 150 mM in an IV bag, 50-250 cc total volume |
| Sodium phosphate buffer | 10-50 mM, pH 5.8 |
| Human albumin | 1 mg/mL |

Human patients manifesting a clinical phenotype of a lysosomal storage disease or disorder are to be treated with a conjugate having a protein or enzyme deficient in the particular disease or disorder. All patients manifest some clinical evidence of excessive or harmful visceral and soft tissue accumulation of storage material in their lysosomes as manifested by varying degrees of functional impairment or worsened health status associated with a particular lysosomal storage disease or disorder. Preferably, enzyme levels are monitored in a patient to confirm the absence or reduced activity of the lysosomal storage disease protein in their tissues. Efficacy is determined by measuring the percentage reduction in urinary excretion of the substrate of the conjugated enzyme over time. The urinary substrate levels in patients are compared to normal excretion values and or levels in untreated patients or the same patients before treatment. Efficacy can also be determined according to the reduced signs and symptoms of any pathology associated with a lysosomal disease. Efficacy can be determined by tissue biopsy and examination of cells and or lysosomes to determine the extent by which substrate or storage material has been reduced. Efficacy can be determined by functional assessments which may be objective or subjective (e.g, reduced pain or difficulty in function, increased muscle strength or stamina, increased cardiac output, exercise endurance, changes in body mass or appearance, etc.). A greater than 25% or 50% reduction in excretion of undegraded substate following therapy with the conjugated agent is a valid means to measure an individual's response to therapy. Data may also be collected measuring the subject conjugated enzyme's activity or presence in tissues before, after and during therapy. Clinical assessment of organ size may be performed as a means of assessing therapeutic efficacy (see, for instance, Hoogerbrugge et al., Lancet 345:1398 (1995)).

Although the invention has been described with reference to the presently preferred embodiments, it should be understood that various modifications can be made without departing from the spirit of the invention.

All publications, patents, patent applications; and web sites are herein incorporated by reference in their entirety to the same extent as if each individual patent, patent application, or web site was specifically and individually indicated to be incorporated by reference in its entirety.

What is claimed is:

1. A method for treating a lysosomal storage disease in a human in need thereof, comprising administering a p97 conjugate to the human, wherein the p97 conjugate comprises a p97 protein or an active fragment or variant thereof covalently linked to a lysosomal storage disease enzyme.

2. The method of claim 1, wherein said p97 protein is a soluble p97 protein.

3. The method of claim 1, wherein said p97 protein is a human p97 protein.

4. The method of claim 1, wherein said p97 protein is a human, soluble p97 protein.

5. The method of claim 1, wherein said p97 protein is a biologically active fragment of a human p97 protein.

6. The method of claim 1, wherein the p97 protein is covalently linked to said agent of interest with a linker.

7. The method of claim 1, where the lysosomal storage disease enzyme is selected from the group consisting of α-L-iduronidase, iduronate-2-sulfatase, heparan-N-sulfatase, α-N-acetylglucosaminidase, arylsulfatase A, galactosylceramidase, acid-α-glucosidase, thioesterase, hexosaminidase A, acid sphingomyelinase, and α-galactosidase.

8. The method of claim 1, where the lysosomal storage disease enzyme is iduronate-2-sulfatase.

9. The method of claim 1, wherein the conjugate is a fusion protein.

10. The method of claim 1, wherein the lysosomal storage disease enzyme is α-L-iduronidase.

* * * * *